(12) United States Patent
Benner et al.

(10) Patent No.: US 8,586,303 B1
(45) Date of Patent: Nov. 19, 2013

(54) IN VITRO SELECTION WITH EXPANDED GENETIC ALPHABETS

(76) Inventors: Steven Albert Benner, Gainesville, FL (US); Zunyi Yang, Gainesville, FL (US)

(*) Notice: Subject to any disclaimer, the term of this patent is extended or adjusted under 35 U.S.C. 154(b) by 0 days.

(21) Appl. No.: 13/493,172

(22) Filed: Jun. 11, 2012

Related U.S. Application Data

(63) Continuation-in-part of application No. 12/999,138, filed on Dec. 15, 2010, and a continuation-in-part of application No. 11/656,317, filed on Jan. 22, 2007, now abandoned, and a continuation-in-part of application No. 12/800,826, filed on May 24, 2010, now abandoned.

(51) Int. Cl.
  *C12Q 1/68* (2006.01)
  *C12P 19/34* (2006.01)

(52) U.S. Cl.
  USPC .................. 435/6.1; 435/91.1; 435/91.2

(58) Field of Classification Search
  USPC ..................... 435/6.1, 91.1, 91.2
  See application file for complete search history.

(56) References Cited

U.S. PATENT DOCUMENTS

| | | | |
|---|---|---|---|
| 5,965,363 A | 10/1999 | Monforte et al. | |
| 6,569,620 B1 | 5/2003 | Gold et al. | |
| 6,613,526 B2 | 9/2003 | Heilig et al. | |
| 6,706,482 B2 | 3/2004 | Smith et al. | |
| 6,716,580 B2 | 4/2004 | Gold et al. | |
| 6,716,583 B2 | 4/2004 | Gold et al. | |
| 6,730,482 B2 | 5/2004 | Gold et al. | |
| 6,855,496 B2 | 2/2005 | Pagratis et al. | |
| 6,933,116 B2 | 8/2005 | Gold et al. | |
| 7,176,295 B2 | 2/2007 | Biesecker et al. | |
| 7,368,236 B2 | 5/2008 | Gold et al. | |
| 7,629,151 B2 | 12/2009 | Gold et al. | |
| 7,709,192 B2 | 5/2010 | Gold et al. | |
| 7,947,447 B2 | 5/2011 | Zichi et al. | |
| 7,964,356 B2 | 6/2011 | Zichi et al. | |
| 8,071,737 B2 | 12/2011 | Gold et al. | |

Primary Examiner — Jezia Riley

(57) ABSTRACT

This invention enables processes for extracting from a mixture of oligonucleotide molecules individuals that bind to a preselected target (aptamers) or catalyze a preselected reaction (xNAzymes) that contain one or more non-standard nucleotides. These pair with their complements in a Watson-Crick geometry with a pattern of hydrogen bonds different from that pairing adenine and thymine, and guanine and cytosine. The processes comprise (a) obtaining this mixture containing non-standard nucleotides within preselected regions, (b) contacting the mixture with a preselected target or one or more reactants for the reaction whose catalysis is desired, (c) separating oligonucleotides having a greater affinity to the target or catalytic effectiveness from the remainder that have less affinity or catalytic effectiveness, and (d) amplifying the separated oligonucleotides. The process exploits PCR conditions that amplify oligonucleotides with less than 5% loss of the non-standard nucleotide per cycle, and processes to determine the sequences of the amplified oligonucleotides.

12 Claims, 17 Drawing Sheets

⇓ Converting Nucleosides

━━━ A T T A C G ━━━

Or

━━━ A T C G C G ━━━

⇓ Cloning and Sequencing (b)
━━━ A T Z P C G ━━━
→                    ←

First Replication ⇓ dNTPs plus dPTP

━━━ A T Z P C G ━━━
━━━ T A P T/C G C ━━━→
                    ←

Second Replication ⇓

━━━ T A P T/C G C ━━━→
←━━ A T T/C A/G C G ━━━

(c)
━━━ A T Z P C G ━━━
→                    ←

First Replication ⇓ dNTPs plus dZTP

━━━ A T Z P C G ━━━
━━━ T A G Z G C ━━━→
                    ←

Second Replication ⇓

━━━ T A G Z G C ━━━→
←━━ A T C G C G ━━━

IN VITRO SELECTION WITH EXPANDED GENETIC ALPHABETS

CROSS REFERENCE TO RELATED APPLICATIONS

This application is a continuation-in-part of the U.S. patent application Ser. No. 12/999,138, filed Dec. 15, 2010 having the title "Polymerase incorporation of non-standard nucleotides", which is co-pending. This application is also a continuation-in-part of the U.S. patent application Ser. No. 11/656,317, filed Jan. 22, 2007 having the title "DNA containing non-standard nucleosides and their precursors", which is co-pending. This application is also a continuation-in-part of the U.S. patent application Ser. No. 12/800,826, filed May 24, 2010 having the title "Non-standard nucleobases implementing the isoguanosine hydrogen bonding patterns", which is co-pending.

STATEMENT OF RIGHTS TO INVENTIONS MADE UNDER FEDERALLY-SPONSORED RESEARCH

This invention was made with government support under HDTRA1-08-1-0052 awarded by the Defense Threat Reduction Agency. The government has certain rights in the invention.

NAMES OF THE PARTIES TO A JOINT RESEARCH AGREEMENT

Not applicable.

INCORPORATION-BY-REFERENCE OF MATERIAL SUBMITTED ON A DISC

None.

BACKGROUND OF THE INVENTION (1) Field of Invention This invention relates to the field of nucleic acid chemistry, more specifically to nucleotide analogs, and still more specifically to "non-standard" nucleotide analogs that, when incorporated into oligonucleotides (DNA or RNA, collectively xNA), present to a complementary strand in a Watson-Crick pairing geometry a pattern of hydrogen bonds that is different from the pattern presented by adenine, guanine, cytosine, and uracil. Most specifically, this disclosure discloses inventive steps that enable the preparation of function oligonucleotides containing non-standard nucleotides that bind to target molecules (called "aptamers") or catalyze reactions (called "xNAzymes") by a process of "in vitro selection" (or IVS). Most specifically, this invention claims processes that comprise the creation of xNA libraries, selecting from those libraries individual xNA molecules that perform the preselected function to generate a fraction of xNA molecules having enhanced performance capabilities, PCR amplifying these with less than 5% loss of the non-standard nucleotide, and determining the sequence of certain of those performing molecules (2) Description of Related Art For two decades, many have sought processes that mimic, in the laboratory, biological evolution to select or evolve DNA or RNA (collectively xNA) molecules that act as ligands, receptors, or catalysts [Ellington & Szostak, 1990][Collett, et. al., 2005][Tuerk & Gold, 1990][Breaker & Joyce, 1994]. This process has been called Systematic Evolution of Ligands by Exponential Enrichment (SELEX), "in vitro selection", or in vitro evolution (collectively referred to as IVS) [Ellington & Szostak 1990] [Tuerk & Gold, 1990]. The xNA ligands and receptors that bind to a preselected target are called aptamers. xNA molecules that catalyze a preselected reaction are called xNAzymes.

As generally practiced, IVS generates aptamers or xNAzymes by the following steps:

(a) A library of nucleic acid (xNA) molecules (typically $10^{14}$ to $10^{14}$ different species) is obtained.

(b) The library is then fractionated to create a fraction that contains molecules better able bind to the preselected target(s), or catalyze the preselected reaction(s), than molecules in the fractions left behind. For example, to generate aptamers, this separation can be done by contacting the library with a solid support carrying the target, washing from the support xNA molecules that do not bind, and recovering from the support xNA molecules that have bound. xNA molecules within the library that bind to the target are said to survive the selection.

(c) The surviving xNAs are then used as templates for the polymerase chain reaction (PCR) process. A low level of mutation may be included in the PCR amplification, creating Darwinian "variation" in an in vitro evolution process.

(d) While it is conceivable that aptamers/xNAzymes having useful binding/catalytic power may emerge in the first "round" of selection, they generally do not. When they do not, the cycle is repeated. With each cycle of fractionation/selection and PCR amplification, the resulting fraction of xNA molecules becomes more enriched in those that bind to the preselected target or catalyze the preselected reaction.

(e) The product xNA aptamer(s) and xNAzyme(s) might be useful if their sequences are not known. However, the utility of these products is nearly always enhanced if their sequences are known, as this allows them to be generated separately. To obtain those sequences, standard IVS procedures generally clone the xNA products in their DNA form (either directly for DNA products, or after conversion to a DNA sequence using reverse transcriptase for RNA products) followed by classical sequencing. Alternatively, next generation sequence can be applied to the mixture of survivors. The elements of this approach are reviewed in many publications [Irvine et al., 1991][Szostak, 1992].

An early example used IVS to obtain oligonucleotides as ligands for reverse transcriptase [Chen & Gold, 1994]. xNA aptamers have now been obtained for many targets, including small molecules [Famulok, 1999], carbohydrates [Sun, et. al., 2010], and peptides [Gopinath, 2007]. Some aptamers discriminate between closely related proteins [Green, et. al., 1996]. Aptamers have been proposed for and used in therapy [Ng, et. al., 2006] [Nimjee, et. al., 2005]. xNAzymes are known to catalyze a wide range of reactions, including RNA cleavage and RNA ligation.

Many advantages anticipated when xNA molecules replace protein molecules have also been realized. For example, xNA aptamers can be reversibly unfolded and refolded, permitting them to be regenerated, giving them longer useful lifetimes and better storage properties [Collett et al., 2005]. xNA aptamers can be inexpensive to prepare on large scale once their sequence has been identified, especially if they can be made using enzymatic amplification tools, such as PCR.

xNA aptamers have other advantages. For example, strategies that allow xNA-based aptamers to directly signal the presence of a bound target are easier to conceive than for antibodies. For example, fluorescent signaling is possible by simply attaching donors and quenchers to specific sites in a DNA sequence [Hiep, et. al., 2010]. More prospectively, but not unreasonably, aptamers might generate electrical readouts when their target is bound [Hayashi, et. al., 2010]; this could reduce enormously the cost of multiplexed diagnostics.

Nevertheless, xNA aptamers have not replaced antibodies, and xNAzymes are not widely used as practical catalysts. While not wishing to be bound by theory, as IVS technology matured, it became clear that the diversity, and binding power of xNA aptamers did not match that of proteins [Proske, et. al., 2005] [Hamula, et. al., 2006], nor did the catalytic power of xNAzymes. These limitations were exemplified and discussed [Li, et. al., 2009]. The limitations of xNA molecules as catalysts has also been discussed [Carrigan, et. al., 2004].

In retrospect, this disappointing outcome might be viewed as unsurprising. Proteins are built from 20 different amino acid building blocks that carry much chemical functionality, including positively charged nitrogens on lysine and arginine, general acid-base functionality on histidine, hydrophobic groups on leucine and others, polarizable binding groups (as on tryptophan and methionine), metal coordinating groups (cysteine, histidine, and others), and so on. Structural biology and mechanistic biochemistry identifies roles for all of these in the binding between proteins and their ligands. In contrast, nucleic acids carry little of this functionality.

Further, with only four building blocks, nucleic acids have fewer motifs for folding than proteins. For example, a G-rich region might lead to a particular "G-quartet", desired to form a specific binding site for a particular target. However, this quartet might be in equilibrium with an alternative folding motif based on G's elsewhere in a sequence involving G:C pairing. The alternative fold need not have any affinity for a target. There are only a limited numbers of interaction types that can be achieved in DNA with just four letters. Further, with low information density arising from four different building blocks, it is difficult to obtain unambiguous folds from standard xNAs. Those attempting to build nanostructures from DNA biobricks have also encountered this as an obstacle to achieving their goals [Smolke 2009]. Further, even if the desired fold is the thermodynamic minimum, it can be kinetically slow to achieve, again because of the low information density in standard xNA.

Of course, stronger affinity is seen with targets having a natural propensity to bind to xNA molecules. For example, aptamers selected to bind HIV integrase, reverse transcriptase, and nucleocapsid proteins have affinities of 10-800, 0.3-20, and 2 nM [Burke et al., 1996] [Allen et al., 1995] [Schneider et al., 1995] [Allen et al., 1996]). Targets with an overall positive charge, complementary to the negative charge of xNA molecules, can also be low, as shown by aptamers to PDGF (0.1 nM [Green et al., 1996]), thrombin (25 nM [Bock et al., 1992])

The limitations of standard DNA and RNA aptamers is evidenced by the number of laboratories that have attempted to surmount the [Battersby, et. al., 1999][Hollenstein, et. al., 2009a][Hollenstein, et. al., 2009b]. Again not wishing to be bound by theory, one hypothesis that holds that the limitations of aptamers and xNAzymes compared to, for example, antibodies and protein enzymes, arise from the relatively little functionality in xNA, compared to proteins.

Pursuing this hypothesis, the Perrin group at the University of British Columbia made DNA where each of the four standard building blocks (G, A, C, and T, or GACT) carries a different functional group [Hollenstein, et al., 2009a][Hollenstein, et al., 2009b]. They report improvement in catalytic power in this system. A decade earlier, the Benner group introduced a single functional group to an ATP aptamer [Battersby, et. al., 1999]. Others have added hydrophilic and hydrophobic groups [Vaught, et. al., 2010] [Zichi, et. al., 2008]. SomaLogic modified uridines at the 5-position of pyrimidines with benzyl, naphthyl, tryptamino, or isobutyl groups, generating SOMAmers (Slow Off rate Modified Aptamers) [Gold, et al., 2010] [Kraemer, et al., 2011].

However, simply functionalizing standard xNA nucleotides (as in SOMAmers) does not greatly expand its diversity of folds. Nor does it increase the information density of the biopolymer. Further, functionalizing GACT encounters a new set of problems. For example, an xNA molecule having a fluorescent group attached to each nucleobase [Brakmann & Nieckchen, 2001] [Brakmann & Lobermann, 2002] are hard to make using xNA polymerases [Ramsay, et. al., 2010]. Further, in ways that are not fully understood, having each nucleobase carry a functional group can cause the DNA to cease to follow "rule based" molecular recognition essential for its genetic roles.

One solution to this impasse involves expanding the number of letters in the DNA alphabet. For example, rearranging hydrogen bond donor and acceptor groups on the nucleobases can increase the number of independently replicable nucleosides in DNA and RNA from four to twelve (FIG. 1) [Switzer, et. al., 1989][Piccirilli, et. al., 1990]. In this "artificially expanded genetic information system" (AEGIS), 12 different nucleotide "letters" pair via six distinguishable hydrogen bonding patterns to give a system that can, in principle, pair, be copied, and evolve like natural DNA, but with higher information density and more functional group diversity.

The potential for using AEGIS to support IVS has been recognized since the proposal of the first AEGIS. Indeed, processes for doing IVS with certain AEGIS-containing nucleotides were claimed by U.S. Pat. No. 5,965,363. However, efforts to implement the process disclosed in that patent have failed. Steps (a) and (b) (above) in the IVS process were possible. Libraries of xNA molecules containing AEGIS components could be prepared, Step (a), and these libraries could be fractionated (Step (b)). However, polymerases were not available to perform PCR on DNA molecules containing multiple AEGIS nucleotides [Sismour, et. al., 2004]. Further, even after polymerases that copied AEGIS nucleotides were obtained, repeated PCR cycling saw their loss [Johnson, et. al., 2004], by perhaps as much as 5% loss per cycle seen when isoguanosine was used to implement the puDDA hydrogen bonding pattern. Efforts to prevent their loss led to DNA molecules with multiple sulfur atoms [Sismour, et. al., 2005], undesirable for many applications. Still other AEGIS components suffered epimerization, which prevented their being routinely copied [Huffer & Benner, 2003].

Further, even if components in a library of AEGIS-containing oligonucleotides could be amplified and the AEGIS components retained, no downstream tools were available to clone the AEGIS-containing xNA aptamers or xNAzymes. Bacteria were not known to accept AEGIS components. Further, no process was available to sequence AEGIS-containing xNA aptamers.

After many years of attempting to do IVS based on libraries of AEGIS-containing oligonucleotides, it is clear that any claims covering an AEGIS-based IVS in the prior art were simply not enabled. This specifically includes the process claimed by U.S. Pat. No. 5,965,363.

BRIEF SUMMARY OF THE INVENTION

This invention provides processes to generate aptamers and xNAzymes that contain nonstandard nucleotide components by in vitro selection (IVS) methods. Specifically, the invention enables steps essential for IVS that have previously not been enabled for xNA molecules containing nonstandard nucleotides: (i) their PCR amplification and (ii) their sequencing. More specifically, this invention generates aptamers and xNAzymes from the nonstandard nucleotides 2-amino-8-(1'-β-D-2'-deoxyribofuranosyl)-imidazo[1,2-a]-1,3,5-triazin-4(8H)one (trivially called dP), 6-amino-5-nitro-3-(1'-β-D-2'-deoxyribofuranosyl)-2(1H)-pyridone (trivially called dZ), and nucleotide analogs carrying the 7-deazaisoguanine (trivially called dB), and isocytosine heterocycles.

BRIEF DESCRIPTION OF THE DRAWINGS

FIG. 5. Strategy for sequencing GACTZP DNA. (a) The positions of Z and P in an amplicon are inferred by a process that converts Z:P pairs into a mixture of T:A pairs and C:G pairs, followed by standard Sanger sequencing. Comparison of the resulting sequences shows only T:A or C:G pairs at sites where T:A or C:G pairs were present in the initial amplicon, but mixtures of T:A and C:G pairs at sites where Z:P pairs were present in the initial amplicon. (b) Manipulation of the concentrations of dPTP without dZTP allows stepwise conversion of Z:P pairs into C:G pairs or into T:A pairs.

Primer-F1:
SEQ ID NO 1
3'-GAAAT*CACTCCCAATTAAGCG-5'

2P-Temp:
SEQ ID NO 2
5'-GCGTAATACGACTCACTATAGACGAPPCTA<u>CTTTAGTGAGGGTTAAT
TCGC</u>-3'

2Z-Temp:
SEQ ID NO 3
3'-<u>CGCATTATGCTGAGTGATATCTGCTZZGATGAAATCACTCCCAATTA
AGCG</u>-5'

Primer-R1:
SEQ ID NO 4
5'-GCGTAATACGACTCAC*TATAG-3'

The * indicates the position of the phosphorothioate linker that prevents complete 3'-exonuclease digestion of the primer. Primer binding sequences are underlined.

(b) Three consecutive non-standard nucleotides copied with Taq, Deep Vent (exo+) and Phusion DNA polymerases.

Primer-F1:
SEQ ID NO 5
3'-GAAAT*CACTCCCAATTAAGCG-5'

3P-Temp:
SEQ ID NO 6
5'-GCGTAATACGACTCACTATAGACACTPPPTACTC<u>ACTTTAGTGAGG GTTAATTCGC</u>-3'

3Z-Temp:
SEQ ID NO 7
3'-<u>CGCATTATGCTGAGTGATATCTGTGA</u>ZZZATGAGTGAAATCACTCC CAATTAAGCG-5'

Primer-R1:
SEQ ID NO 8
5'-GCGTAATACGACTCAC*TATAG-3'

(c) Four consecutive non-standard nucleotides copied with Taq, Deep Vent (exo+) and Phusion DNA Primer-F1:
SEQ ID NO 9
3'-GAAAT*CACTCCCAATTAAGCG-5'

4P-Temp:
SEQ ID NO 10
5'-GCGTAATACGACTCACTATAGACACTPPPPTACTC<u>ACTTTAGTGAGG GTTAATTCGC</u>-3'

4Z-Temp:
SEQ ID NO 11
3'-<u>CGCATTATGCTGAGTGATATCTGTGA</u>ZZZZATGAGTGAAATCACTCC CAATTAAGCG-5'

Primer-R1:
SEQ ID NO 12
5'-GCGTAATACGACTCAC*TATAG-3'

Figure 7:
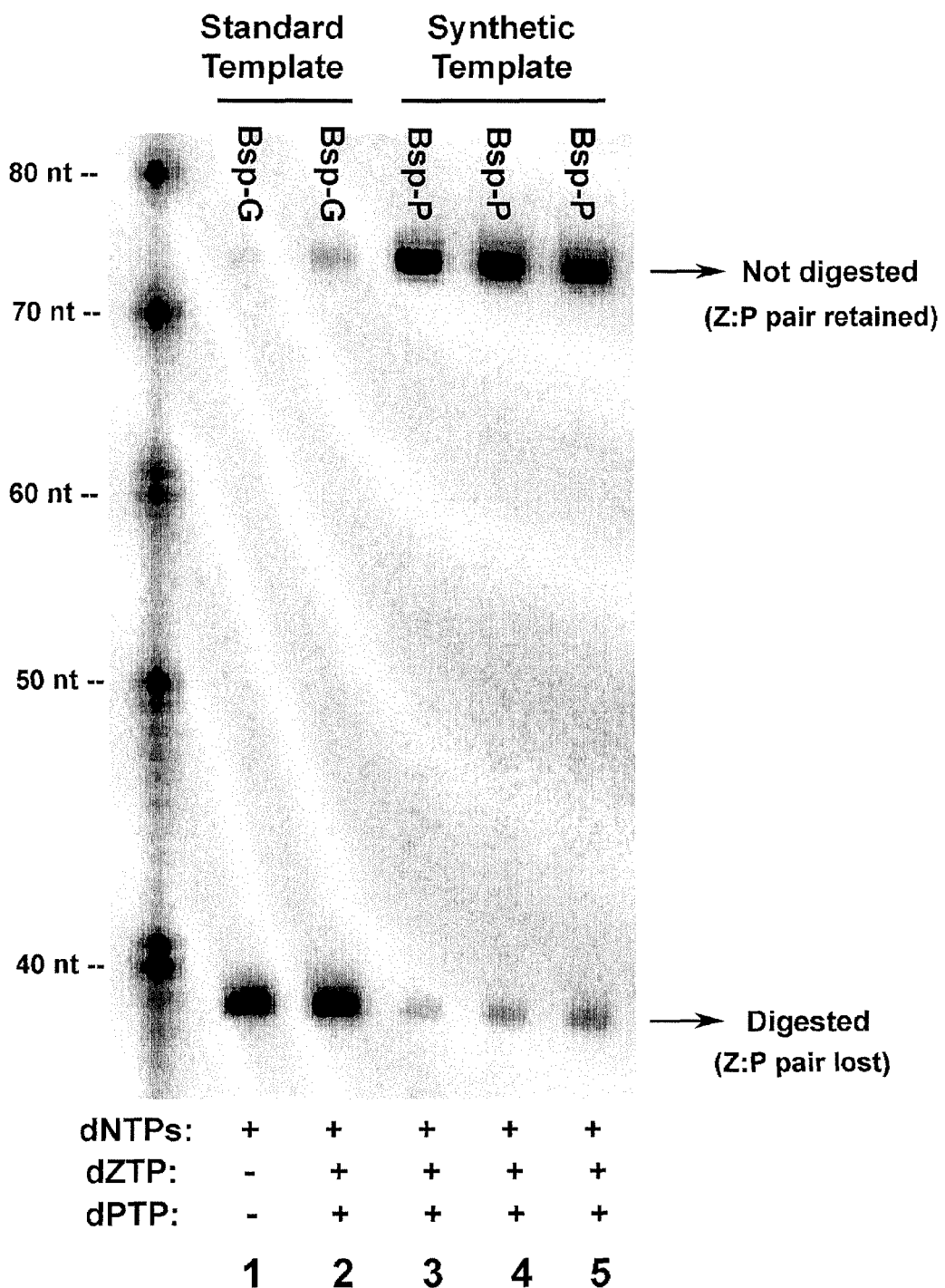

FIG. 7. PCR amplification of the GACTZP DNA and measurement of the fidelity of Z:P pair in six-letter PCR. Standard template (Bsp-G, Table 1) and synthetic template (Bsp-P, Table 1) were amplified using Taq DNA polymerase in 1× ThermoPol buffer (pH 8.0), followed by digestion with Bsp120I endonuclease. Four standard dNTPs (each 0.2 mM), dZTP=0.2 mM, and dPTP=0.2 mM.

Lanes 1 and 2: Standard template was amplified $10^4$ fold using Taq, without (lane 1) and with (lane 2) dZTP and dPTP;
Lanes 3, 4, and 5: Synthetic template, $10^3$ (line 3), $10^4$ (line 4), and $10^5$ (line 5) fold amplification, with both dZTP and dPTP;
Not digested: Indicates the fraction of PCR product that retained Z:P pair, and therefore resisted endonuclease digestion;
Digested: Indicates the fraction of PCR product that was digested, because it lost the Z:P pair.

DESCRIPTION OF INVENTION

Figure 1:
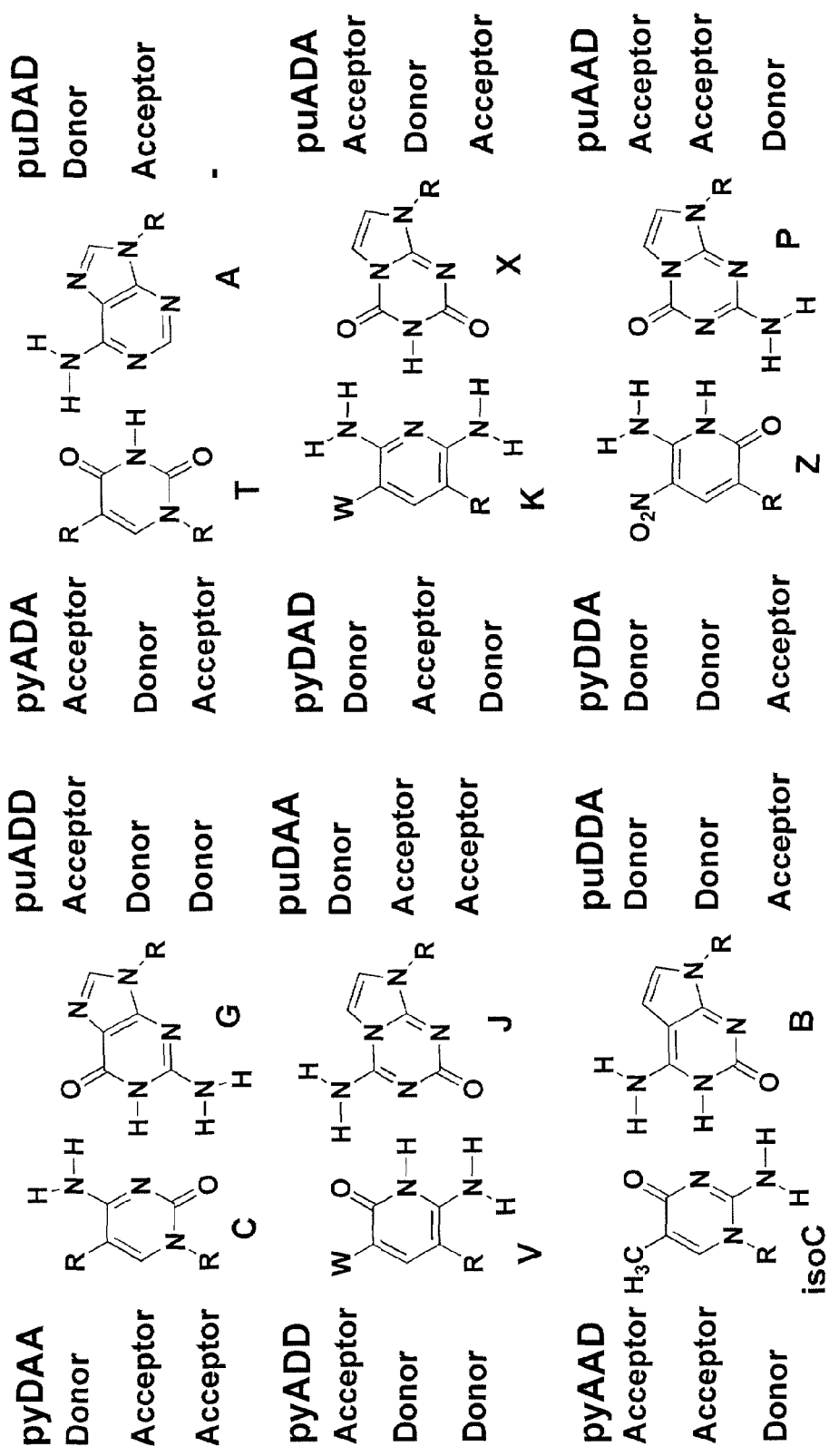
FIG. 1 Watson-Crick pairing rules follow two rules of complementarity: (a) size complementarity (large purines pair with small pyrimidines) and (b) hydrogen bonding complementarity (hydrogen bond donors, D, pair with hydrogen bond acceptors A). Rearranging D and A groups on various heterocycles supports an artificially expanded genetic information system (AEGIS). AEGIS nucleobases can also be functionalized at the position indicated by the "R" in these structures. Thus, AEGIS offers a solution to the limitations of aptamers by increasing the number of building blocks, and functionalizing an expanded set of building blocks.

Definition of Non-Standard Components of an Artificially Expanded Genetic Information System This application teaches a distinction between the hydrogen-bonding pattern (in the nomenclature in FIG. 1, pyDAD, for example) and the heterocycle that implements it. Thus, the pyADA hydrogen-bonding pattern is implemented by thymidine, uridine, and pseudouridine. The puDDA hydrogen bonding pattern is implemented by both the heterocycle isoguanosine and 7-deaz-isoguanosine. Heterocycles to implement any particular pre-selected hydrogen-bonding pattern are preferred depending on their chemical properties, for example, high chemical stability or low tautomeric ambiguity. The pyADA, pyDAA, puADD, and puDAD hydrogen bonding patterns are said to be "standard" hydrogen bonding patterns, and to form with their appropriate complement "standard base pairs". Other hydrogen bonding patterns are said to be "non-standard", and to form with their appropriate complement "non-standard base pairs".

Relevant Prior Art

IVS processes with nucleotides that implement standard hydrogen bonding patterns have been known for many decades (see references above). From this art, those of ordinary skill might also be able to perform several of the steps of an IVS process for DNA that contains non-standard nucleotides as well, specifically:

(a) The art does teach an ordinarily skilled artisan how to obtain a library of nucleic acid (xNA) molecules incorporating nucleotides carrying various non-standard nucleobases, such as Z, P, 5-methyl-isoC, isoG, and various analogs of isoG, including B. Phosphoramidites suitably protected to support solid phase synthesis of these are known in the art [Yang, et. al., 2010]. Several are commercially available. Solid phase synthesis of libraries of DNA molecules is likewise known, involving the use of mixtures of phosphoramidites or split-and-pool synthesis. Libraries of RNA molecules can be obtained by transcribing libraries of encoding DNA molecules.

(b) The art does teach an ordinarily skilled artisan how to fractionate the library to separate molecules that bind preselected target(s), or catalyze preselected reaction(s), from molecules that do not. Fractionation for IVS with non-standard nucleotides is not materially different from that used in standard IVS. Further, a variety of variants of selection processes, and various applications of the derived species have been covered by various patents, including:

U.S. Pat. No. 8,071,737: Nucleic acid ligand complexes. This invention covers a method for preparing a therapeutic or diagnostic complex comprised of a nucleic acid ligand and a lipophilic compound or non-immunogenic, high molecular weight compound U.S. Pat. No. 7,964,356: Method for generating aptamers with improved off-rates. This invention covers methods for producing aptamers and photoaptamers having slower dissociation rate constants than are obtained using SELEX and photoSELEX methods.

U.S. Pat. No. 7,947,447: Method for generating aptamers with improved off-rates. This invention covers improved SELEX methods for producing aptamers that are capable of binding to target molecules and improved photo-SELEX methods for producing photoreactive aptamers.

U.S. Pat. No. 7,709,192: Nucleic acid ligand diagnostic biochip. This invention covers nucleic acid ligand "biochips", consisting of a solid support to which one or more specific nucleic acid ligands is attached in a spatially defined manner.

U.S. Pat. No. 7,629,151: Method and apparatus for the automated generation of nucleic acid ligands. This invention covers a method and device for performing automated SELEX.

U.S. Pat. No. 7,368,236: Methods of producing nucleic acid ligands. This invention covers methods for the identification and production of improved nucleic acid ligands based on the SELEX process.

U.S. Pat. No. 7,176,295: Systematic evolution of ligands by exponential enrichment: blended SELEX. This invention covers a method for generating blended nucleic acid ligands containing non-nucleic acid functional units.

U.S. Pat. No. 6,933,116: Nucleic acid ligand binding site identification. This invention covers a nucleic acid ligand for use as a diagnostic reagent for detecting the presence or absence of a target molecule in a sample, and a diagnostic reagent.

U.S. Pat. No. 6,855,496: Truncation SELEX method. This invention covers a method for identifying nucleic acid ligands by the SELEX method wherein the participation of fixed sequences is eliminated or minimized.

U.S. Pat. No. 6,730,482: Modified SELEX processes without purified protein. This invention covers a method for obtaining nucleic acid ligands against target proteins without directly purifying the target proteins.

U.S. Pat. No. 6,716,583: Methods of producing nucleic acid ligands. This invention covers methods for the identification and production of improved nucleic acid ligands based on the SELEX process.

U.S. Pat. No. 6,716,580: Method for the automated generation of nucleic acid ligands. This invention covers a method and device for performing automated SELEX.

U.S. Pat. No. 6,706,482: Conditional-selex. This invention covers a method for producing nucleic acid ligands that generate a signal, or cause a decrease in the level of a signal, in the presence of a target molecule U.S. Pat. No. 6,613,526: Systematic evolution of ligands by exponential enrichment: tissue selex.

This invention covers methods to create high-affinity oligonucleotide ligands to complex tissue targets, specifically nucleic acid ligands having the ability to bind to complex tissue targets, U.S. Pat. No. 6,569,620: Method for the automated generation of nucleic acid ligands. This invention covers a method and device for performing automated SELEX.

Each of these is incorporated in its entirety herein by reference. Each of these could also be applied to IVS based on AEGIS components, if only the steps not enabled in the art were to be enabled.

Processes that are Absent in the Prior Art

Missing from the art for standard IVS and all of its variants, and not obvious to those of ordinary skill in the art, are the remaining steps in the IVS process. Specifically:

(c) Absent from the art prior to the priority date of this application, PCR amplification using AEGIS components is not available. For the instant invention, AEGIS PCR amplification is made available in U.S. patent application Ser. No. 12/999,138, having the title: Polymerase incorporation of non-standard nucleotides which is herein incorporated in its entirety by reference, with respect to pyDDA:puAAD pairs. This application provides for processes that PCR amplify DNA containing G, A, C, T, Z, and P nucleotides. AEGIS PCR amplification is made available in U.S. patent application Ser. No. 12/800,826, which describes variants of isoguanine with lower amounts of minor tautomeric forms, which is herein incorporated in its entirety by reference, with respect to pyAAD:puDDA pairs.

(d) Also absent in the prior art are processes to do the repeated cycling needed to obtain useful aptamers and DNAzymes for selection survivors containing AEGIS components, as this requires PCR amplification of nucleic acid analogues containing AEGIS components.

(e) Also absent in the prior art are procedures to efficiently sequence DNA containing AEGIS components. While methods in the art, including dideoxy sequencing, might be applied to DNA containing AEGIS components, the challenges associated with this application have to date prevented any successful AEGIS IVS. A workable method of sequencing is disclosed here, and is based on U.S. patent application Ser. No. 12/999,138, which is herein incorporated in its entirety by reference. This application provides for processes that convert Z:P pairs in DNA into A:T pairs and/or C:G pairs, or isoC:7-deazaisoG pairs into T:A pairs, enabling a process for efficiently sequencing aptamers/xNAzymes built from G, A, C, T, Z, and P nucleotides. This method for sequencing employs the following steps:

(a) Perform amplification under conditions that convert Z:P pairs sometimes to C:G pairs and sometimes to T:A bases;

(b) Shotgun clone the products of that amplification, now built entirely from standard nucleotides;

(c) Sequence the cloned material using high throughput DNA sequencing; and (d) Align and compare the sequences recovered.

In this "converting nucleosides" strategy (FIG. 5a), two populations of standard DNA are generated from one precursor of GACTZP DNA. Sites that originally held Z in the precursor hold either C or T in the converted sequence. This generates a "C" call half of the time, and a "T" call the other half of the time. Similarly, sites that originally held P will generate either a "G" call or an "A" call. Sites that originally held G, A, C, and T will give uniform calls in all of the sequences returned. Thus, the sequence of the precursor and the positions of Z and P in that sequence can be inferred (FIG. 5a).

DESCRIPTION OF THE PREFERRED EMBODIMENTS

The presently preferred AEGIS components to support IVS are nucleosides that implement the pyDDA and puAAD hydrogen bonding patterns. For DNA, presently preferred implementation of the pyDDA hydrogen bonding pattern is the nucleoside analog 6-amino-5-nitro-3-(1'-(3-D-2'-deoxyribofuranosyl)-2(1H)-pyridone. The presently preferred implementation of the puAAD hydrogen bonding pattern is the nucleoside analog. These are trivially named dZ and dP; their ribonucleoside analogues are preferred to implement IVS based on an RNA-like scaffold.

For the pyAAD hydrogen-bonding pattern, the presently preferred nucleobase embodiments are isocytosine and pseudocytosine disclosed in U.S. Pat. No. 7,741,294, which is incorporated in its entirety herein by reference. For the puDDA hydrogen-bonding pattern, the presently preferred nucleobase embodiment is 7-deazaisoguanine.

EXAMPLES

Example 1

Step (a). Obtaining a Library of Nucleic Acid Molecules

Phosphoramidites, Triphosphates, and Polymerases.

Protected phosphoramidites of the non-standard nucleosides dZ (protected as the O-NPE ether) and dP were obtained from the Foundation for Applied Molecular Evolution (www.ffame.org, Nitroaminopyridone-dZ (Cat. #DZ-ZY001), Imidazoaminopyrimidone-dP (Cat. #DP-ZY001). Phosphoramidites of the standard nucleotides were obtained from Glen Research. GACT DNA was obtained from IDT (Coralville Iowa). Other reagents were from Promega and Sigma-Aldrich, and used as received.

Oligonucleotides containing dZ and dP were synthesized using standard phosphoramidite chemistry on an ABI 394 DNA synthesizer on controlled pore glass supports. Following synthesis, oligonucleotides containing dZ were first treated with 1 M of DBU in anhydrous acetonitrile to remove the O-protection group (O—NPE either). The remaining protecting groups were then removed in aqueous concentrated ammonia overnight at 55° C.

Example 2

Step (b). Selection

The goal of this in vitro selection experiment was to obtain a DNA enzyme that catalyzes the cleavage of a single ribonucleotide link (designated as "rA") in an oligonucleotide that holds the library to the support, a selection first performed for standard nucleotides by Breaker and Joyce [Breaker & Joyce 1995]. The selection principle is simple: members of the library able to catalyze this cleavage release themselves from a solid support, and appear in an eluate. To support this selection, the following DNA molecules were prepared, several with ribo-A (rA) embedded in the sequence:

```
Std-N40-88mer
                                       SEQ. ID. NO. 49
5'-GTGCCAAGCTTACCGTCAC---N(40)---GAGATGTCGCCATCTCT

TCCTATAGTGAG-

A = 10; T = 13; G = 10; C = 14; N = 40

Biotin-rA-SELEX-43mer
                                       SEQ. ID. NO. 50
5'-Biot-CTGCAGAATTCTAATACGACTCACTATrAGGAAGAGATGGCG

AC

2Biotin-rA-SELEX-43mer
                                       SEQ. ID. NO. 50
5'-2-Biot-CTGCAGAATTCTAATACGACTCACTATrAGGAAGAGATGG

CGAC

Forw-riboA-SELEX-43mer
                                       SEQ. ID. NO. 50
5'-CTGCAGAATTCTAATACGACTCACTATrAGGAAGAGATGGCGAC Forw-dA-SELEX-43mer
                                       SEQ. ID. NO. 50
5'-CTGCAGAATTCTAATACGACTCACTATrAGGAAGAGATGGCGAC (43mer)

SEQ. ID. NO. 51
3'-CAGCGGTAGAGAAGGATATCACTCAGCATAATCTTAAGACGTC-5'

Rev-SELEX-19mer
                                       SEQ. ID. NO. 52
5'-GTGCCAAGCTTACCGTCAC-3' (19mer)

SEQ. ID. NO. 53
3'-CACTGCCATTCGAACCGTG-5' (15mer)

Rev-SELEX-15mer
                                       SEQ. ID. NO. 54
5'-GTGCCAAGCTTACCG-3' (15mer)
```

```
Comp-SELEX-48mer
                                       SEQ. ID. NO. 55
5'-GAGATGTCGCCATCTCTTCCTATAGTGAGTCGTATTAGAATTCTGCA

G

SEQ. ID. NO. 56
3'-CAGCGGTAGAGAAGGrATATCACTCAGCATAATCTTAAGACGTC-5'

SEQ. ID. NO. 49
5'-GTGCCAAGCTTACCGTCAC-N(40)-GAGATGTCGCCATCTCTTCC

TATAGTGAG

SEQ. ID. NO. 52
5'-GTGCCAAGCTTACCGTCAC
```

Libraries with dZ and dP were prepared with 4%, 8%, 12%, 16%, and 33% dZ+dP

```
                                       SEQ. ID. NO. 57
5'-GTGCCAAGCTTACCGTCAC-N/Z/P(40)-GAGATGTCGCCATCTCT

TCCTATAGTGAG
```

Reagents:
1. Standard phosphoramidites were used in equal amounts in the synthesis: Bz-dA, Ac-dC, dmf-dG, and dT. For libraries containing dZ and dP, varying amounts of the protected dZ and dP phosphoramidites were used.
2. Activator: 0.25 M 4,5-dicyanoimidazole (DCI) in acetonitrile (Glen Research)
3. Cap Mix A: THF/Pyridine/Ac2O;
4. Cap Mix B: 6.5% DMAP in THF
5. Oxidizing Solution: 0.02M $I_2$ in THF/Pyridine/$H_2$O;
6. Deblocking Mix: 3% DCA/DCM
Modification of Cycle Procedure (with Capping, 0.2 m CPG).
1. The coupling wait time was increased from 25 sec to 30 sec.
2. The capping wait time was increased from 5 sec to 6 sec.
3. The oxidation wait time was increased from 15 sec to 18 sec.
4. For deblocking using DCA (3%) in DCM, wait time was increased from 35 sec to 70 sec.
Modification the Cycle Procedure without Capping Step
1. Delete the steps (from step 46 to 51) for capping reagents (Cap A and Cap B);
2. Extend the delivery time of 0.002 M $I_2$ from 8 s to 10 s (step 55);
The synthesis was executed in three steps. In the first step, the 3'-29 mer was prepared with capping. In the second, the N(40) library was synthesized without capping. In the third, the remaining 19 nucleotides were added with capping, with the final DMT removed.
The same approach was used to prepare the library with Z and P in the randomized region, one gram of equal molar of A/G/C/T mixture was dissolved in 12.5 mL of anhydrous acetonitrile to give a 0.1M of total amidites concentration (0.25 M for each amidite).
Deprotection and Ethanol Precipitation of ZIP Containing Oligo:
Modified Procedure:
1. The column used to support the synthesis was dried with air.
2. The CPG-bound oligonucleotide was treated with triethylamine-acetonitrile (1:1 v/v, 1.5 mL) for 1 hour. The supernatant was removed and another 1.5 mL of triethylamine-acetonitrile (1:1 v/v) was added for another 12-16 h at 25° C.
3. After the second step supernatant was removed.
4. 1.0 mL of DBU in anhydrous $CH_3CN$ (1M, 0.37 mL of DBU dissolve in 2.2 mL of $CH_3CN$) was added, and the mixture was shaken at room temperature for 15 to 20 hours.

5. CH$_3$CN was removed using speed vacuum.

6. The residue was incubated with fresh concentrated NH4OH (deprotection reagent) (1 mL) at 55° C. overnight. If dZ was protected by Ac, 2 mL of AMA (40% MeNH$_2$ in H$_2$O/concentrated NH$_4$OH=1/1, v/v) was added at 65° C. for 5-10 min (at 55° C., for 1020 min).

7. The mixture was cooled at room temperature for about 10 min.

8. The supernatant (leaving all the CPG behind) was transferred into a plastic centrifuge tube (15 mL), and the residue (CPG) was washed with 1 mL of H$_2$O; the washings were combined.

9. 10% volume of 3M NaOAc (200 μL, pH=5.0~6.0) was added to the above solution, followed by 2.5 volume of cold EtOH (5 mL, pre-cooled at −20° C.). A white precipitate formed.

10. The mixture was incubated at −20° C. for hours/11.

11. The DNA was recovered by centrifugation for 10 minutes at 4° C. (4,000 rpm).

12. The supernatant was removed, and the residue was washed with 1 mL room-temperature 95% or 80% ethanol to remove the NaOAc.

13. The DNA was recovered by centrifugation (10 minutes, 4° C., 4,000 rpm).

14. The supernatant was removed and the DNA pellet was dried.

Step 2: PCR Amplification of the Library

A primer to library ratio of 4:1 is preferred. After 20 cycles of primer extension at 72° C. for 5 min, 33.7% of primer was converted into full-length product with standard N40 library, 16% of primer was converted into full-length product with ZP(8%)_N40 library, and 11% of full-length product for the ZP(16%)_N40 library.

4° C. forever. Primer extension conditions for primer/library ratio=10/1: one cycle of 94° C. for 1 min; 10, 20, and 30 cycles of (94° C. for 30 s, 60° C. for 30 s, 72° C. for 5 min); 72° C. for 5 min, then 4° C. forever.

First Round of Selection

In vitro selection was performed by the method of Breaker and Joyce [Breaker & Joyce 1995] to select for oligonucleotides that cleave the single ribonucleotide in a substrate. The first round of selection used a library containing 8% of Z+P in the N(40) random region. Radiolabeling the library allowed the monitoring of the selection process.

Materials and Reagents:

Dynabead® M-270 Streptavidin (Invitrogen) is a set of uniform super-paramagnetic beads of 2.8 μm in diameter with a streptavidin monolayer covalently coupled to the hydrophilic bead surface. Dynabead® M-270 Streptavidin beads are dissolved in phosphate buffered saline (PBS, pH 7.4) and contains 10 mg (6-7×10$^8$) Dynabead per mL. One Dynabead contains ca. 7×10$^5$ Streptavidin molecules, implying means that 1 mL of Dynabead suspension contains 4.55×10$^{14}$ streptavidin molecules per mL of suspension. The typical binding capacity for 1 mg of Dynabead was about 200 pmole of biotinylated single stranded oligonucleotides.

Binding and washing (B&W) Buffer: 2× Buffer A (100 mM HEPES (pH 7.4), 2M NaCl, 1 mM EDTA);

Removing complementary strand: 0.2 M of NaOH;

Neutralizing Buffer: 50 mM HEPES (pH 7.4), 1 mM EDTA;

Reaction Buffer: 1× Buffer B (1M NaCl, 50 mM HEPES, 2 mM MgCl$_2$, pH 7.4).

Bead Preparation: Wash & Binding Protocol:

1. The beads were resuspended in the original vial by vortexing or rotation.

2. Beads (0.1 m, 1 mg) were transferred to a 1.5 mL tube.

|  | Primer/Library (Standard) | | Primer/Library with 8% Z + P | | Primer/Library with 16% Z + P) | | |
| --- | --- | --- | --- | --- | --- | --- | --- |
| Components | A (5/1) | B (10/1) | C (5/1) | D (10/1) | E (5/1) | F (10/1) | Final Conc. |
| ddH$_2$O | 5.7 μL | 5.7 μL | 5.7 μL | 5.7 μL | 5.7 μL | 5.7 μL | Final (15 μL) |
| $^{32}$P-Forw-rA-SELEX-43 (2 μM) | 2 μL | 4 μL | 2 μL | 4 μL | 2 μL | 4 μL | 0.267 or 0.533 μM |
| Forw-rA-SELEX-43 (100 μM) | 0.3 μL | 0.6 μL | 0.3 μL | 0.6 μL | 0.3 μL | 0.6 μL | 2 μ or 4 μM |
| ddH$_2$O | 2.3 μL | | 2.3 μL | | 2.3 μL | | |
| Std-N40-88mer-Cap (10 μM) | 0.75 μL | 0.75 μL | | | | | 0.5 μM |
| ZP8%-N40-88mer-Cap (10 μM) | | | 0.75 μL | 0.75 μL | | | 0.5 μM |
| ZP16%-N40-88mer-Cap (10 μM) | | | | | 0.75 μL | 0.75 μL | 0.5 μM |
| Six-Nucleotide Mix of 10× dA, T, G/TPs (1 mM of each) dCTP (2 mM) dZTP (0.5 mM) dPTP (6 mM) | 1.5 μL | 1.5 μL | 1.5 μL | 1.5 μL | 1.5 μL | 1.5 μL | 0.1 mM of each 0.2 mM 0.05 mM 0.6 mM |
| 10× ThermoPol Buffer (pH = 8.0) | 1.5 μL | 1.5 μL | 1.5 μL | 1.5 μL | 1.5 μL | 1.5 μL | 1× |
| JumpStart Taq (2.5 units/μL, Sigma) | 1 μL | 1 μL | 1 μL | 1 μL | 1 μL | 1 μL | 0.167 (U/μL) |

Note: 1. The primer to library ratio are about 5/1 or 10/1.

1× ThermoPol Reaction Buffer (20 mM Tris-HCl, 10 mM (NH$_4$)$_2$SO$_4$, 10 mM KCl, 2 mM MgSO$_4$, 0.1% Tritonx-100, pH 8.0 at 25° C.).

Primer extension conditions for primer/library ratio=5/1: one cycle of 94° C. for 1 min; 5, 10, and 20 cycles of (94° C. for 30 s, 60° C. for 30 s, 72° C. for 5 min); 72° C. for 5 min, then 3. The tube was placed on a magnet for ca. 2 minutes, collecting the beads on the tube wall.

4. The supernatant was removed with a pipette while the tube was on magnet.

5. The tube was removed from magnet; binding and washing buffer (0.4 mL of 2× Buffer A) as added along inside of the tube, where the beads were collected and resuspended.

6. Steps 3-5 were repeated for a total of 3 washes.
7. The beads were then resuspended in 2× Buffer A to final concentration of 5 mg/mL (0.2 mL of 2× Buffer A)
8. An equal volume of biotinylated DNA in ddH$_2$O (0.2 mL) was added to dilute 2× Buffer A from 2 M NaCl to 1M NaCl for optimal binding (to give a total volume of 0.4 mL per Library).
9. Incubation continued for 15 to 30 minutes at room temperature with gentle rotation of the tube on Thermomixer R (Eppendorf) with 500 rpm.
10. The tube was placed in a magnet for 2-3 minutes and discarded the supernatant.
11. The biotinylated DNA coated beads were washed 4 times with 1× Buffer A (0.2 mL of Buffer A).
12. The beads were resuspended in 0.2 mL of NaOH (0.2 M, pre-cooled to 4 degree) for 0.5 min.
13. The tube was placed in a magnet for 1 min and collected the supernatant.
14. The NaOH wash was repeated for three times.
15. The beads were washed with 0.2 mL of Neutralize Buffer (50 mM HEPES (pH 7.4), 1 mM EDTA) twice.
16. The beads were incubated with 0.15 mL of 1× Buffer B (1M NaCl, 50 mM HEPES, 2 mM MgCl$_2$, pH 7.4) using gentle rotation on Thermomixer R (Eppendorf) with 500 rpm at 25 degree.
17. The surviving DNAzymes were collected by extraction with a magnet.
18. The selection process was repeated with incubation times of 20 min, 60 min, and 120 min.
19. Each sample was centrifuged for 1 min to pellet trace carry-over beads and transferred 150 µL of eluate to a new tube (left beads behind).
20. The DNA was cleaved off beads by incubation in aqueous NaOH (0.2 M, 85° C., 20 min).
21. The oligo in each sample was quantitated using the Liquid Scintillation Analyzer (Tri Carb 2800 TR, PerkinElmer).
22. PAGE Gel (10%) was used to analyze the process of the selection:
The process was monitored by following the radiation arising from 5'-phosphorus-32 labeling of the oligonucleotides.
PCR Amplification of the Survivors
The survivors (Neutral Wash I and II) from the first-round of selection (containing 8% ZP) were PCR amplified and agarose gel purified. Significant amount of amplicon (about 110 bp in length) were generated after 15 cycles of PCR amplification. However, after 18 and 21 cycles of PCR, longer PCR amplicons (about 125 bp in length) were generated. There is no detectable primer dimer and PCR artifacts.

Example 3

Step (c). Polymerase Amplification of Z- and P-Containing DNA

Triphosphates dZTP and dPTP were obtained from the Foundation for Applied Molecular Evolution (www.ffame.org, dZTP (Cat. # DZTP-ZY101), dPTP (Cat. # DPTP-ZY102)). Polymerases were obtained from New England Biolabs or from other sources. GACT DNA was obtained from IDT (Coralville Iowa). Other reagents were obtained from Promega and Sigma-Aldrich, and used as received. The procedures followed those published in [Yang, et al., 2011], which is incorporated herein in its entirety by reference.
Primer Extension on GACTZP DNA.
To demonstrate that GACTZP primer extension through multiple Ps and Zs works, primer (5'-$^{32}$P-radiolabeled Primer-F1 or Primer-R1, 0.2 pmole, see Table 1 for primer sequences) was diluted with unlabeled primer (4 pmole, final concentration 70 nM), and the primer mixture was annealed to one of a number of templates containing multiple consecutive non-standard nucleobases (dP or dZ, 6 pmole, final concentration 100 nM) in 1× ThermoPol polymerase reaction buffer (pH=8.0 at room temperature) or 1×HF Phusion buffer (pH=8.3 at room temperature) by heating (96° C., 5 min) followed by slow cooling (0.5 h) to room temperature. dNTPs (N=GACT, final 0.1 mM for each), or dNTPs, dZTP and dPTP (final 0.1 mM for each) were then added at room temperature. The mixture was pre-heated at 72° C. for 30 seconds. Extension was initiated by adding Taq (2.5 units), Deep Vent (exo$^+$, 2 units), or Phusion (1 unit) DNA polymerase to give a final volume of 60 µL. The primer was extended at 72° C. and aliquots (7 µL) were taken from each reaction at time intervals (1, 2, 4, 8, and 16 min), quenched by PAGE loading/quench buffer (10 µL, 10 mM EDTA in formamide). Samples were resolved by electrophoresis using a 16% PAGE (with 7 M urea). A MolecularImager was used to analyze the products. FIG. 6 shows the results.

TABLE 1

| | Oligonucleotides | |
|---|---|---|
| Primer-F1: | 3'-GAAATCACTCCCAATTAAGCG-5' | SEQ ID NO 13 |
| 2G-Temp: | 5'-GCGTAATACGACTCACTATAGACGAGGCTACTTTAGTGAGGGTTAATTCGC-3' | SEQ ID NO 14 |
| 1P-Temp: | 5'-GCGTAATACGACTCACTATAGACGAPCGTACTTTAGTGAGGGTTAATTCGC-3' | SEQ ID NO 15 |
| 2P-Temp: | 5'-GCGTAATACGACTCACTATAGACGAPPCTACTTTAGTGAGGGTTAATTCGC-3' | SEQ ID NO 16 |
| 3P-Temp: | 5'-GCGTAATACGACTCACTATAGACACTPPPTACTCACTTTAGTGAGGGTTAATTCGC-3' | SEQ ID NO 17 |
| 4P-Temp: | 5'-GCGTAATACGACTCACTATAGACACTPPPPTACTCACTTTAGTGAGGGTTAATTCGC-3' | SEQ ID NO 18 |
| 4G-Temp: | 5'-GCGTAATACGACTCACTATAGACACTGGGGTACTCACTTTAGTGAGGGTTAATTCGC-3' | SEQ ID NO 19 |
| 2C-Temp: | 3'-CGCATTATGCTGAGTGATATCTGCTCCGATGAAATCACTCCCAATTAAGCG-5' | SEQ ID NO 20 |
| 1Z-Temp: | 3'-CGCATTATGCTGAGTGATATCTGCTZGCATGAAATCACTCCCAATTAAGCG-5' | SEQ ID NO 21 |
| 2Z-Temp: | 3'-CGCATTATGCTGAGTGATATCTGCTZZGATGAAATCACTCCCAATTAAGCG-5' | SEQ ID NO 22 |
| 3Z-Temp: | 3'-CGCATTATGCTGAGTGATATCTGTGAZZZATGAGTGAAATCACTCCCAATTAAGCG-5' | SEQ ID NO 23 |
| 4Z-Temp: | 3'-CGCATTATGCTGAGTGATATCTGTGAZZZZATGAGTGAAATCACTCCCAATTAAGCG-5' | SEQ ID NO 24 |

TABLE 1-continued

Oligonucleotides

| | |
|---|---|
| 4C-Temp: | 3'-CGCATTATGCTGAGTGATATCTGTGACCCCATGAGT<u>GAAATCACTCCCAATTAAGCG</u>-5' SEQ ID NO 25 |
| Primer-R1: | 5'-<u>GCGTAATACGACTCACTATAG</u>-3' SEQ ID NO 26 |
| Primer-F2: | 3'-<u>CAGTATCGACAAAGGACACACGCT</u>-5' SEQ ID NO 27 |
| ZZ-2P: | 5'-<u>GACACTAGTAGCACTCACTATACG</u>TGACTCPTCACZZAGTGCPACTACG<u>GTCATAGCTGTTTCCTGTGTGCGA</u>-3' SEQ ID NO 28 |
| PP-2Z: | 3'-<u>CTGTGATCATCGTGAGTGATATGC</u>ACTGAGZAGTGPPTCACGZTGATGC<u>CAGTATCGACAAAGGACACACGCT</u>-5' SEQ ID NO 29 |
| Primer-R2: | 5'-<u>GACACTAGTAGCACTCACTATACG</u>-3' SEQ ID NO 30 |
| Primer-F3: | 3'-<u>TATGCAACGCTAGCGAGGAAGGAC</u>-5' SEQ ID NO 31 |
| Bsp-Z: | 5'-<u>CTAGGACGACGGACTGCCTATGAGAGACATGA</u>*GGGCC*ZGGTACCATCG<u>ATACGTTGCGATCGCTCCTTCCTG</u>-3' SEQ ID NO 32 |
| Bsp-P: | 3'-<u>GATCCTGCTGCCTGACGGATACTCT</u>CTGTACT*CCCGG*PCCATGGTAGC<u>TATGCAACGCTAGCGAGGAAGGAC</u>-5' SEQ ID NO 33 |
| Bsp-C: | 5'-<u>CTAGGACGACGGACTGCCTATGAGAGACATGA</u>*GGGCC*CGGTACCATCG<u>ATACGTTGCGATCGCTCCTTCCTG</u>-3' SEQ ID NO 34 |
| Bsp-G: | 3'-<u>GATCCTGCTGCCTGACGGATACTCT</u>CTGTACT*CCCGG*GCCATGGTAGC<u>TATGCAACGCTAGCGAGGAAGGAC</u>-5' SEQ ID NO 35 |
| Primer-R3: | 5'-<u>CTAGGACGACGGACTGCCTATGAG</u>-3' SEQ ID NO 36 |

PCR Amplification of the GACTZP DNA.

Figure 2A:
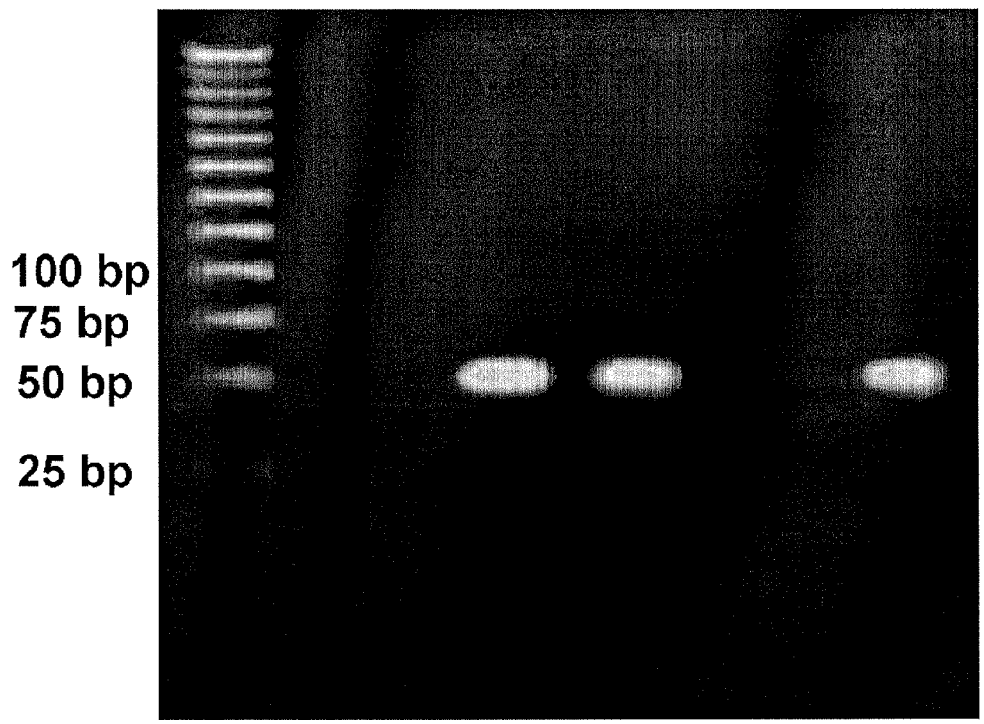
FIG. 2. Agarose gel (3%) resolving amplicons from "six-letter" GACTZP PCR with standard templates and synthetic templates containing multiple consecutive dPs. Lane 1: Control without template; Lane 2: Amplification of standard template, without dZTP and dPTP; Lane 3: Amplification of standard template, with dZTP and dPTP; Lanes 4 and 6: Amplification of synthetic template, without dZTP and dPTP; Lanes 5 and 7: Amplification of synthetic template, with dZTP and dPTP. dNTPs (0.1 mM for each), dZTP (0.05 mM) and dPTP (0.6 mM). M: 25 bp marker. See Examples for conditions.
Figure 2B:
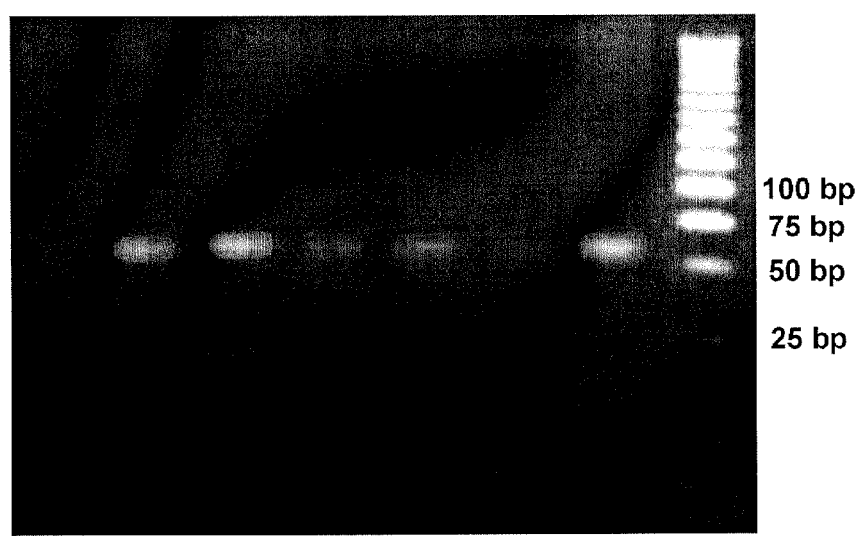
Figure 2C:

Six-letter PCR amplification of GACTZP DNA containing multiple consecutive non-standard nucleobases (2P-Temp, 3P-Temp, and 4P-Temp, final 0.5 nM, Table 1) was carried out in 1× ThermoPol reaction buffer (pH=8.0 at room temperature, for Deep Vent (exo+) and Taq DNA polymerase, respectively), or 1×HF Phusion buffer (pH=7.0 at room temperature, for Phusion DNA polymerase), 0.5 μM of each Primer-F1 and Primer-R1, dA,T,G/TPs (each 0.1 mM), dCTP (0.2 mM), dZTP (0.05 mM), dPTP (0.6 mM), and 0.05 unit/μL of DNA polymerase (Taq) or 0.02 unit/4 (Deep Vent (exo+) and Phusion, respectively) on the DNAEngine Peltier Thermal Cycler (Bio-Rad) in a total volume of 50 μL. The following PCR conditions were used: one cycle of 95° C. for 2 min; followed by 21 cycles of (95° C. for 20 s, 58° C. for 25 s, 72° C. for 3 min); and finally 72° C. for 10 min. Upon the completion of PCR, samples (10 μL) were taken from each PCR mixture, mixed with 6× agarose loading dye (2 Promega), and analyzed on a 3% agarose gel. FIG. 2 shows the results.

Figure 3A:
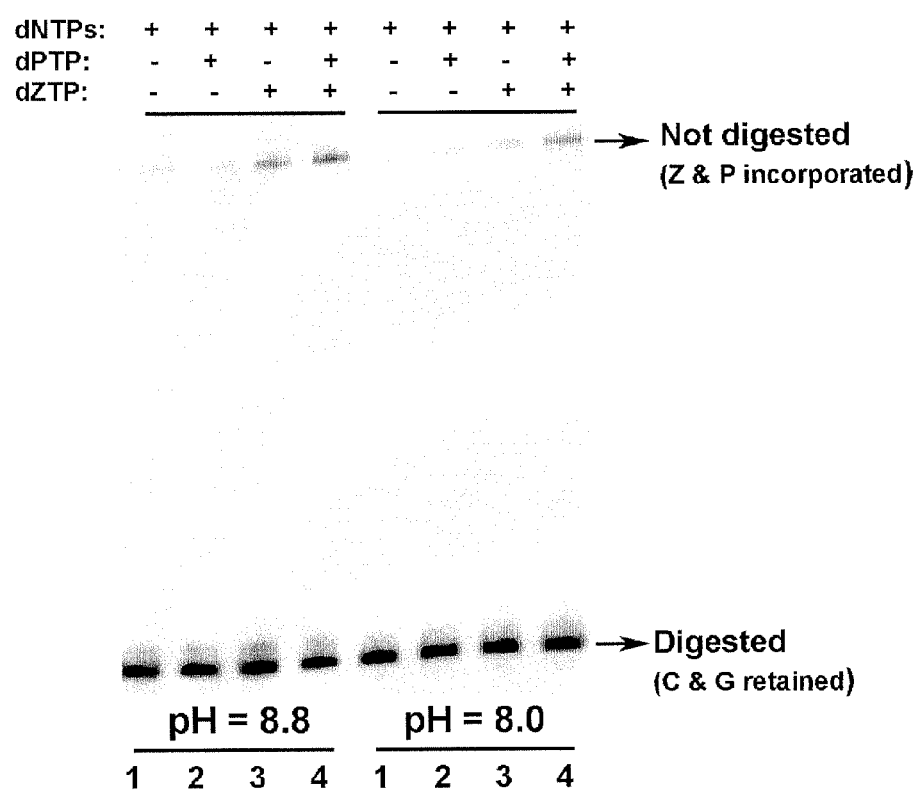
FIG. 3. Interconversions between Z:P and C:G (or T:A) pairs.
(a) Measuring the "forward" mutation converting C:G pairs into Z:P pairs using digestion with the Bsp120I restriction endonuclease. Standard oligonucleotide (Bsp-G, Table 1) containing the Bsp120I recognition sequence (5'-GGGCCC-3') were 1000 fold amplified using Taq DNA polymerase at pH=8.8 or 8.0 with standard dNTPs (0.2 mM of each) with or without dZTP and dPTP. The amplicons were digested by endonuclease (Bsp120I). See Examples for conditions.
Lane 1: Amplification in the absence of both dZTP and dPTP;
Lane 2: Amplification with dPTP (0.2 mM);
Lane 3: Amplification with dZTP (0.2 mM);
Lane 4: Amplification with both dZTP and dPTP (0.2 mM for each),
Not digested: indicates the fraction of PCR product resistant to endonuclease digestion, indicating retention of the Z:P pair.
Digested: indicates the fraction of PCR product was digested, indicating replacement of the Z:P pair by a C:G pair.
(b) Assessing the "reverse" mutation of Z:P pairs to give C:G and T:A using restriction endonuclease. Two complementary synthetic templates (Bsp-Z and Bsp-P, Table 1) containing 5'-GGGCCZ-3' and 3'-CCCGGP-5', were 1000 fold amplified using Taq with standard dNTPs (200 µM), dZTP and dPTP (with various concentration, lane 1 (20 µM), lane 2 (10 µM), lane 3 (5 µM)), then, PCR amplicon were digested by endonuclease (Bsp120I). See Examples for conditions.
(c) Indicates the part of the PCR product where Z is replaced by C (left) and P is replaced by A and G (right) using restriction endonuclease digestion. Single-stranded synthetic oligonucleotide containing either 5'-GGGCCZ-3' (left, lane 1, Bsp-Z) or 3'-CCCGGP-5' (right, lane 2, Bsp-P), was 1000 fold amplified using Taq with only four standard dNTPs (0.2 mM) in 1× ThermoPol reaction buffer (pH 8.8 at room temperature). Then, PCR amplicon was digested by endonuclease (Bsp120I). See Methods and Materials for details.
(d) Proposed mechanism for pH-dependent mismatching of Z with G.

Measuring the Low Levels of Mutation Interconverting Z:P, C:G and T:A Pairs:

The presently preferred level of mutation in standard PCR is less than 5% replacement per cycle, and preferably less than 2% per cycle. No prior art has achieved this. To demonstrate these low levels of replacement here, the "forward" mutation converting C:G pairs into Z:P pairs was detected using digestion with the restriction endonuclease (Bsp120I). Eight parallel PCRs were performed in 1× ThermoPol buffer at two different pHs (8.8 and 8.0 at 25° C.). The PCR mixture contained identical amounts of primers, (Primer-F3 (5 pmole) and Primer-R3 (1 pmole of 5'-$^{32}$P-labeled primer and 4 pmole of non-$^{32}$P-labeled primer), each 250 nM final), template (Bsp-G, 0.25 nM final), four standard dNTPs (0.2 mM each), and JumpStart Taq DNA polymerase (0.075 unit/μL, Sigma). Two non-standard nucleotide triphosphates, dZTP and dPTP (each 0.2 mM), were absence or present in each PCR mixture (see FIG. 3a for details). The PCR mixture (20 μL of total volume) were cycled using the following conditions: one cycle of 95° C. for 1 min; followed by 26 cycles of (95° C. for 30 s, 55° C. for 30 s, 72° C. for 1 min); and finally 72° C. for 10 min. After PCR amplification, samples (5 μL) were taken from each PCR mixture, mixed with PAGE loading/quench buffer (7 μL, 10 mM EDTA in formamide), and resolved by electrophoresis using 10% PAGE (7 M urea). The gel was analyzed using MolecularImager software. The results shown all primers were consumed and PCR amplicon was produced with the expected length. Then, another 1 μL of PCR mixture was digested with Bsp120I (0.5 μL, final 0.5 units/μL) in 1× Buffer B (10 mM Tris-HCl, 10 mM MgCl$_2$, 0.1 mg/ml BSA, pH 7.5) at 37° C. for 20 hours (104 of reaction volume). Additional 0.5 μL of Bsp120I was added to the digestion mixture and incubated for another 20 hours. The digestion products were resolved on 10% PAGE gel (7 M urea) and visualized by autoradiography (see FIG. 3a for results).

Measuring "Reverse" Mutation of Z:P Pair to Give C:G and T:A Pair Using the Restriction Endonuclease (Bsp120I).

Figure 3B:
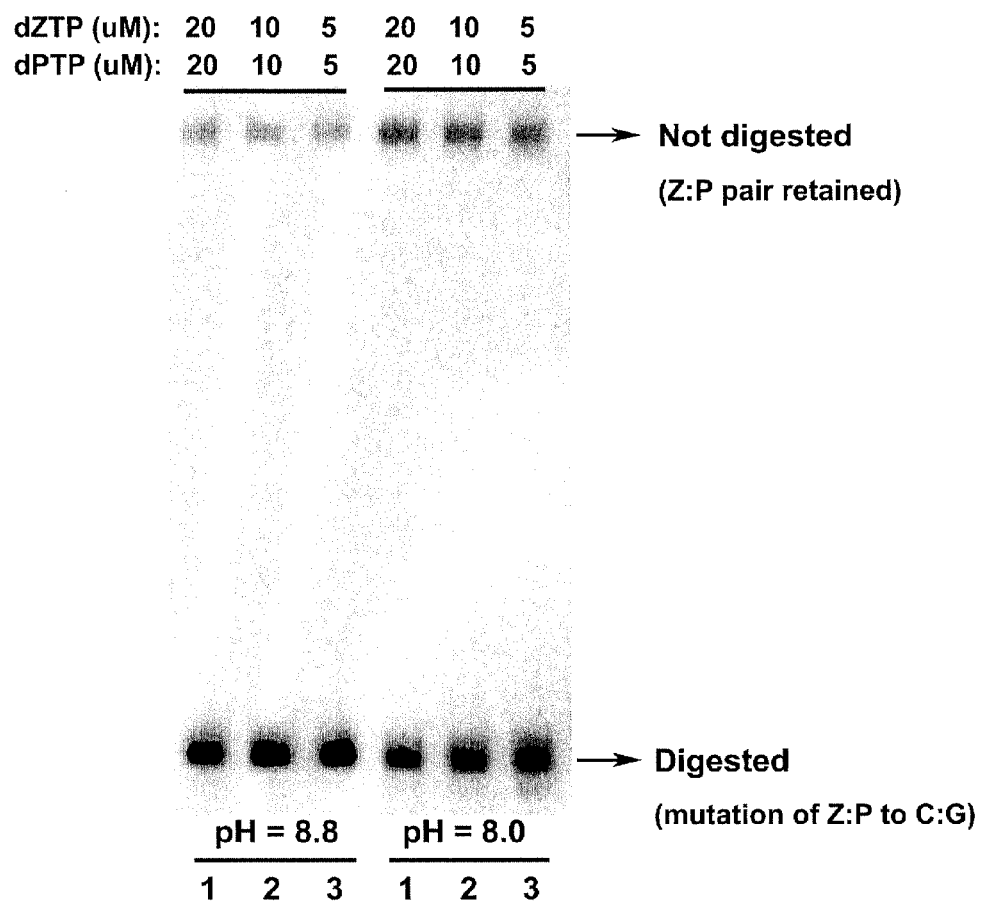

Six parallel PCRs were performed in 1× ThermoPol buffer at two different pHs (8.8 and 8.0, measured at 25° C.). The PCR mixture contained identical amounts of primers, (Primer-F3 (5 pmole) and Primer-R3 (1 pmole of 5'-$^{32}$P-labeled primer and 4 pmole of non-$^{32}$P-labeled primer), each 250 nM final), synthetic templates (Bsp-Z and Bsp-P, Table 1, each 0.25 nM final), four standard dNTPs (200 μM each), various amount of dZTP and dPTP (20 μM (lane 1), 10 μM (lane 2), and 5 μM (lane 3), respectively, FIG. 3b), and JumpStart Taq DNA polymerase (0.075 unit/4, Sigma). The PCR mixture (20 μL of total volume) was cycled (26 rounds of 95° C. for 30 s, 55° C. for 30 s, 72° C. for 1 min). Upon the completion of PCR amplification, 1 μL of PCR mixture was digested with BsP120I (0.5 μL, final 0.5 units/μL) in 1× Buffer B (10 mM Tris-HCl, 10 mM MgCl$_2$, 0.1 mg/ml BSA, pH 7.5) at 37° C. for 20 hours (10 μL of reaction volume). Additional 0.5 μL of Bsp120I was added to the digestion mixture and incubated for another 20 hours. The digestion products were resolved on 10% PAGE gel (7 M urea) and visualized by autoradiography (see FIG. 3b for results).

Figure 3C:
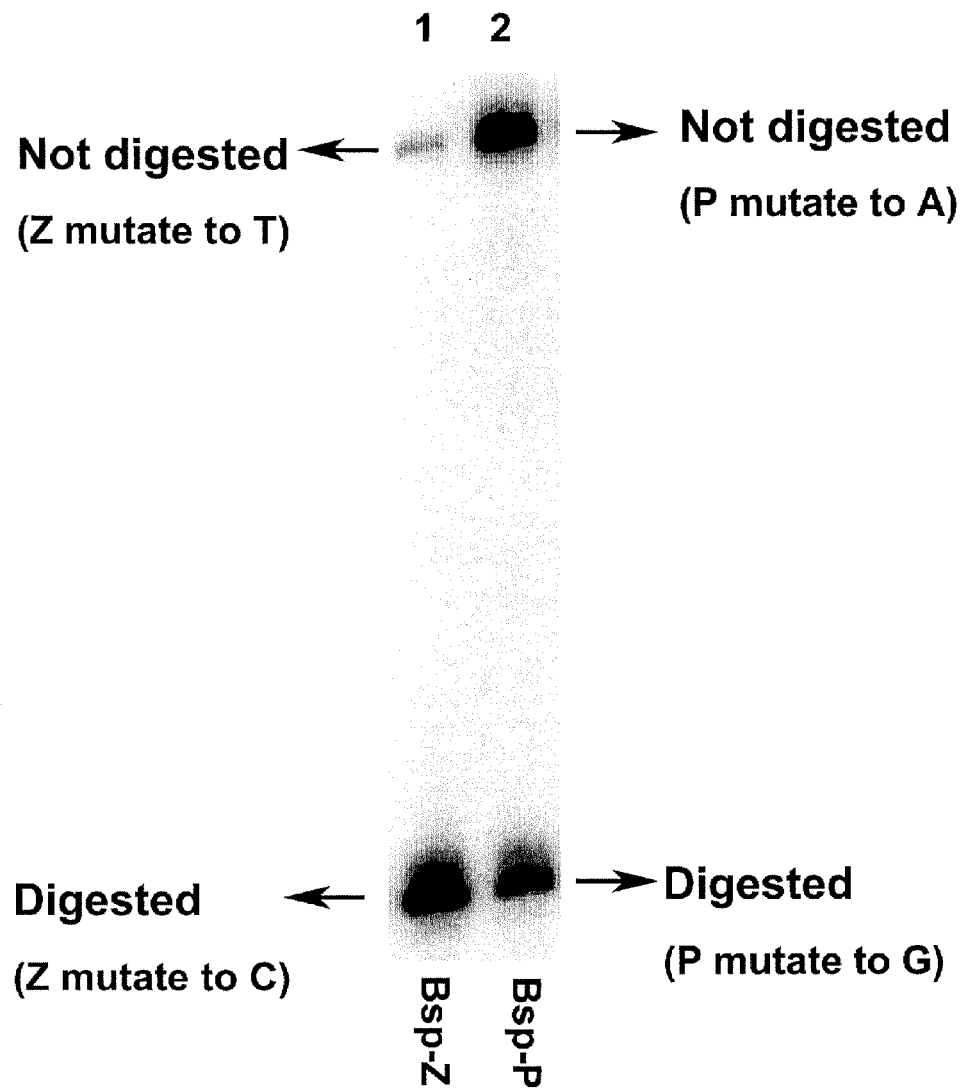
Figure 3D:
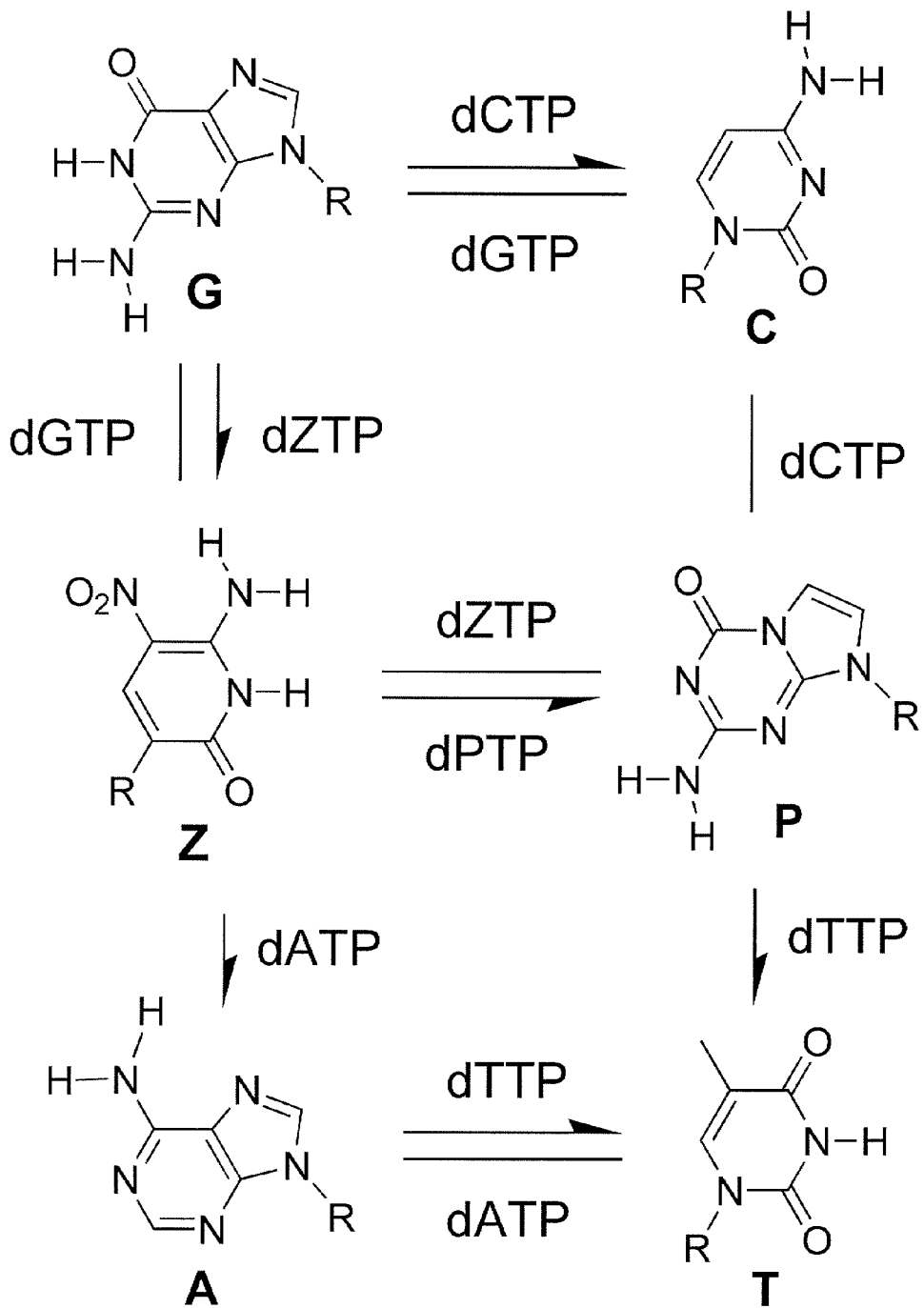

Measuring Mutation of Z to C or T and P into A or G with Restriction Endonuclease Bsp120I In 1× ThermoPol reaction buffer (pH 8.8 at 25° C.) and 0.2 mM of each four standard dNTPs (without dZTP and dPTP), single-stranded synthetic template Bsp-Z (FIG. 3c, lane 1) or Bsp-P (FIG. 3c, lane 2) was 1000 fold amplified with primers (Primer-F3 and Primer-R3) using JumpStart Taq DNA polymerase (0.08 unit/4, Sigma). Upon the completion of PCR amplification, 1 µL of PCR mixture was digested with Bsp120I (1 µL, final 1 units/µL) in 1× Buffer B at 37° C. for 20 hours (10 µL of reaction volume). Then, additional 0.5 µL of Bsp120I was added to the digestion mixture and incubated for another 20 hours. The digestion products were resolved on 10% PAGE gel (7 M urea) and visualized by autoradiography (see FIG. 3c for results).

Measuring the Retention and Mutation of Z:P Pair in Optimized Six-Letter PCR.

Figure 4:
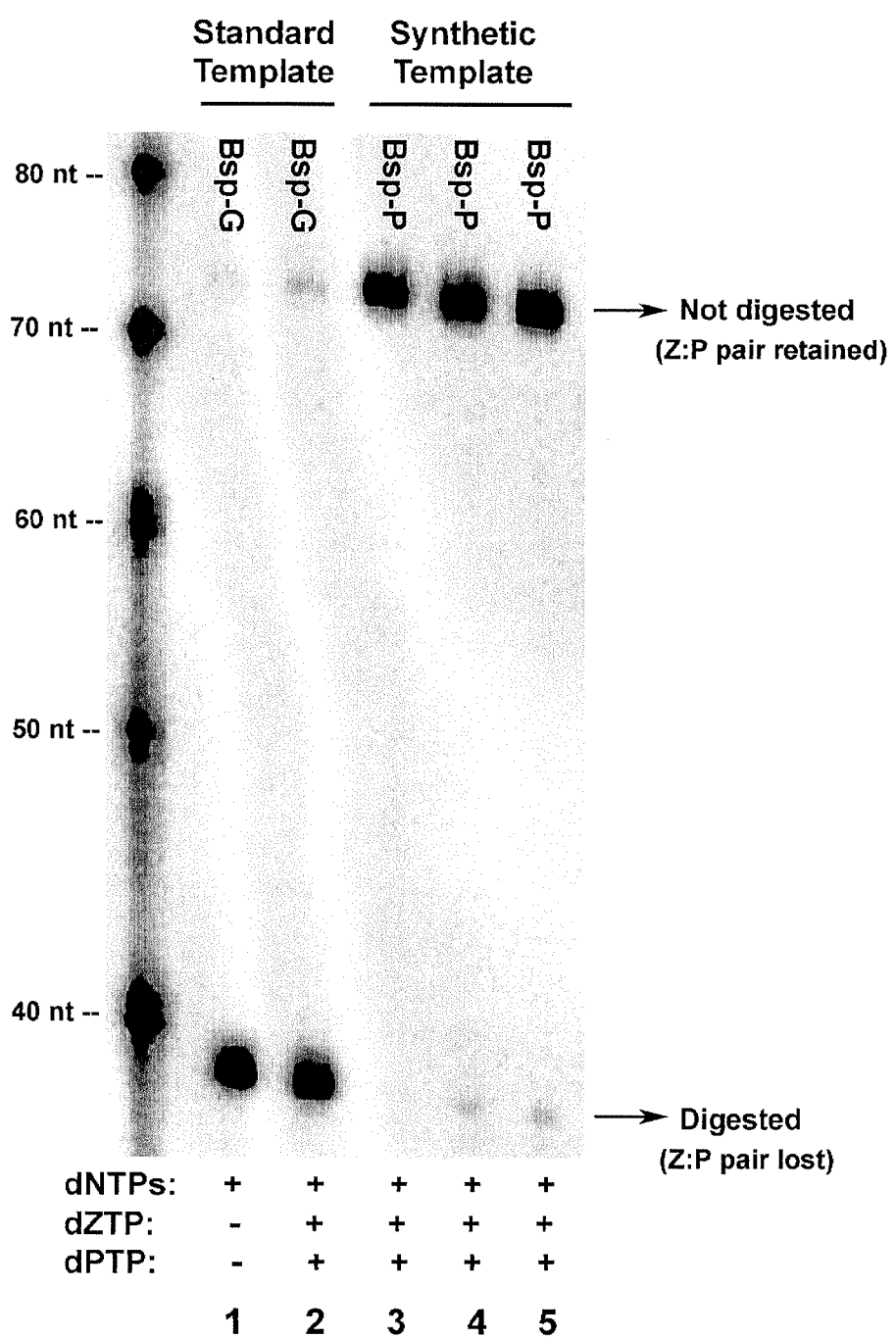
FIG. 4. Measuring the retention and loss of Z:P pairs in six-letter PCR.
Standard template (Bsp-G, Table 1) and synthetic template (Bsp-P, Table 1) were amplified using Taq DNA polymerase under 1× Thermopol buffer (pH 8.0), followed by endonuclease digestion (Bsp120I). dA,T,G/TPs=0.1 mM, dCTP=0.4 mM, dZTP=0.05 mM, and dPTP=0.6 mM. See Examples for conditions.
Lanes 1 and 2: Standard template was amplified $10^4$ fold using Taq, without (lane 1) and with (lane 2) dZTP and dPTP; Lanes 3, 4, and 5: Synthetic template, $10^3$ (lane 3), $10^4$ (lane 4), and $10^5$ (lane 5) fold amplification, with both dZTP and dPTP;
Not digested: Indicates the part of the PCR product that retained Z:P pair, and therefore resisted endonuclease digestion.
Digested: Indicates the part of the PCR product that was digested, and therefore lost the Z:P pair.
Figure 6A:
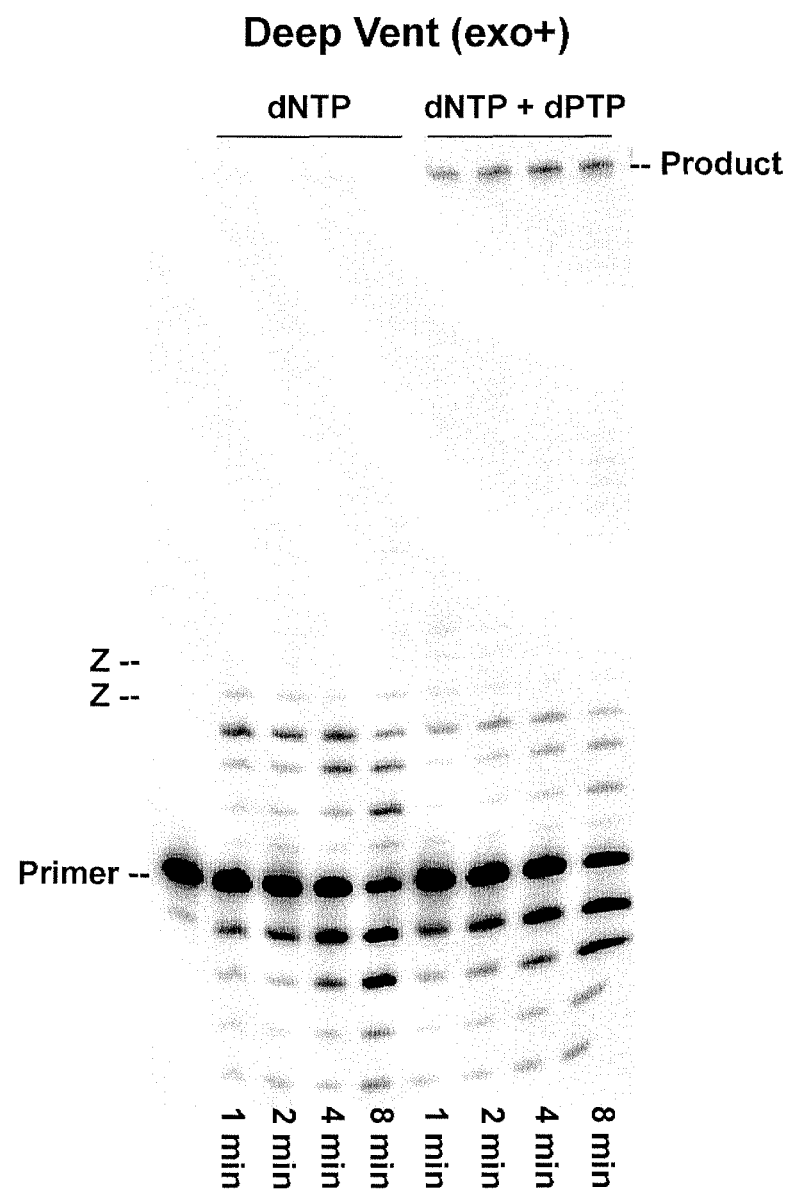
FIG. 6. Polymerase extension that reads through multiple consecutive non-standard nucleobases. Various polymerases were challenged to incorporate consecutive non-standard nucleotides opposite consecutive non-standard complements in 1× Thermopol reaction buffer (for Taq and Deep Vent (exo⁺), pH 8.0, measured at room temperature) or 1× Phusion HF buffer (for Phusion at pH ca. 8.3) at 72° C. for the times indicated on the gels (1 to 16 min).
Negative control (−): dNTPs (each 0.1 mM).
Positive control (+): dNTPs (each 0.1 mM) and dZTP (0.1 mM, left gel) or dPTP (0.1 mM, right gel).
(a) Two consecutive non-standard nucleotides copied with Deep Vent (exo⁺) DNA polymerase.
Figure 6A:
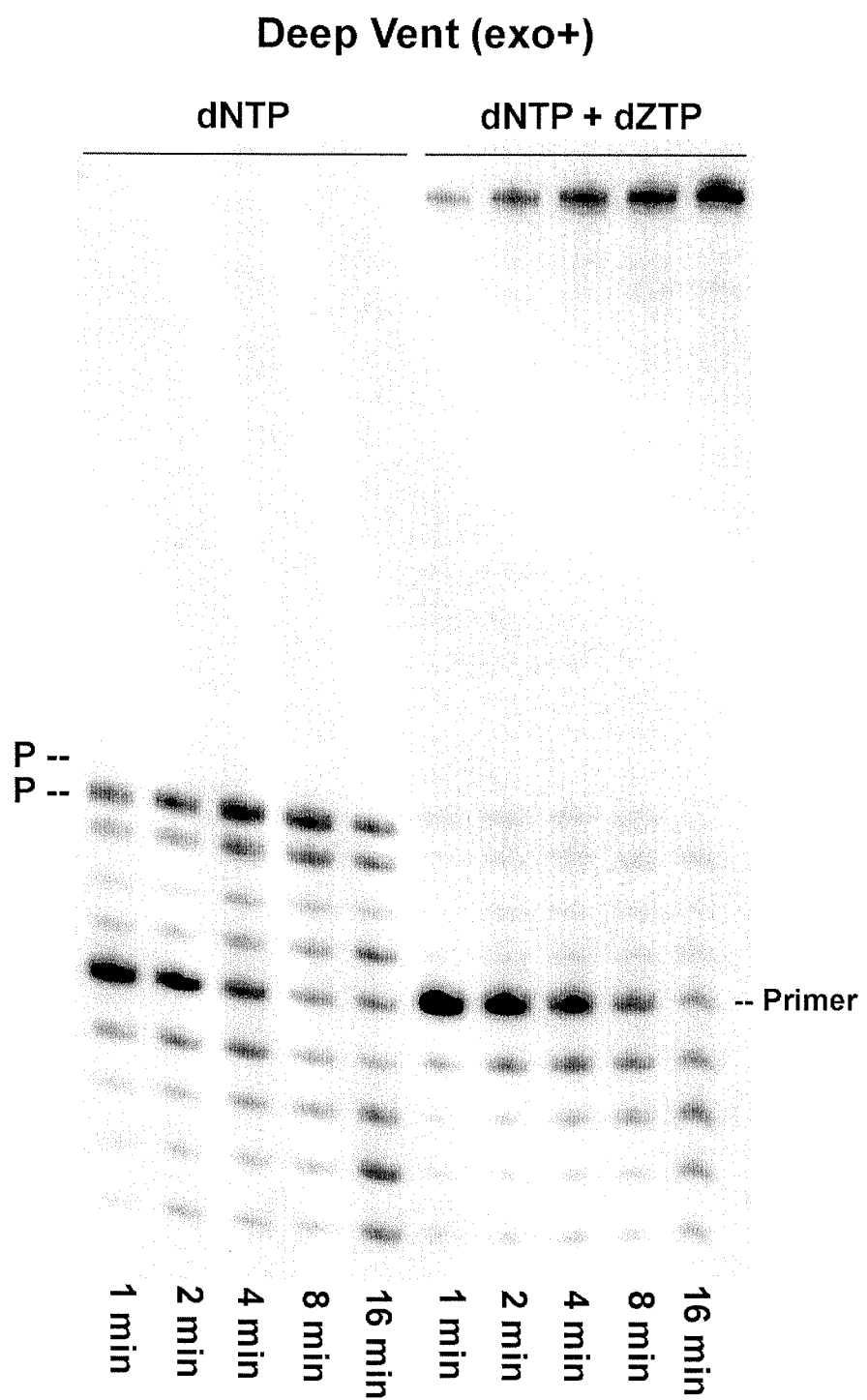
Figure 6B:
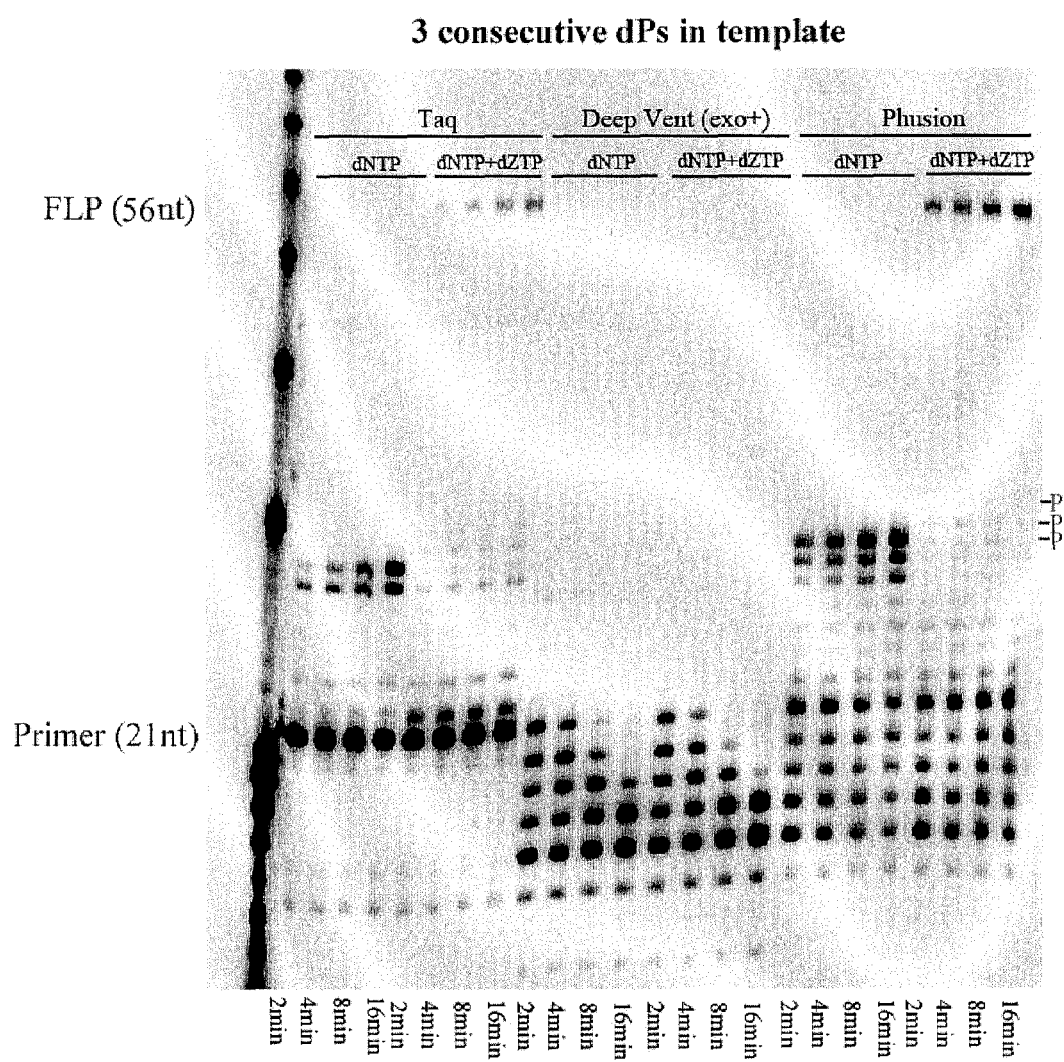
Figure 6B:
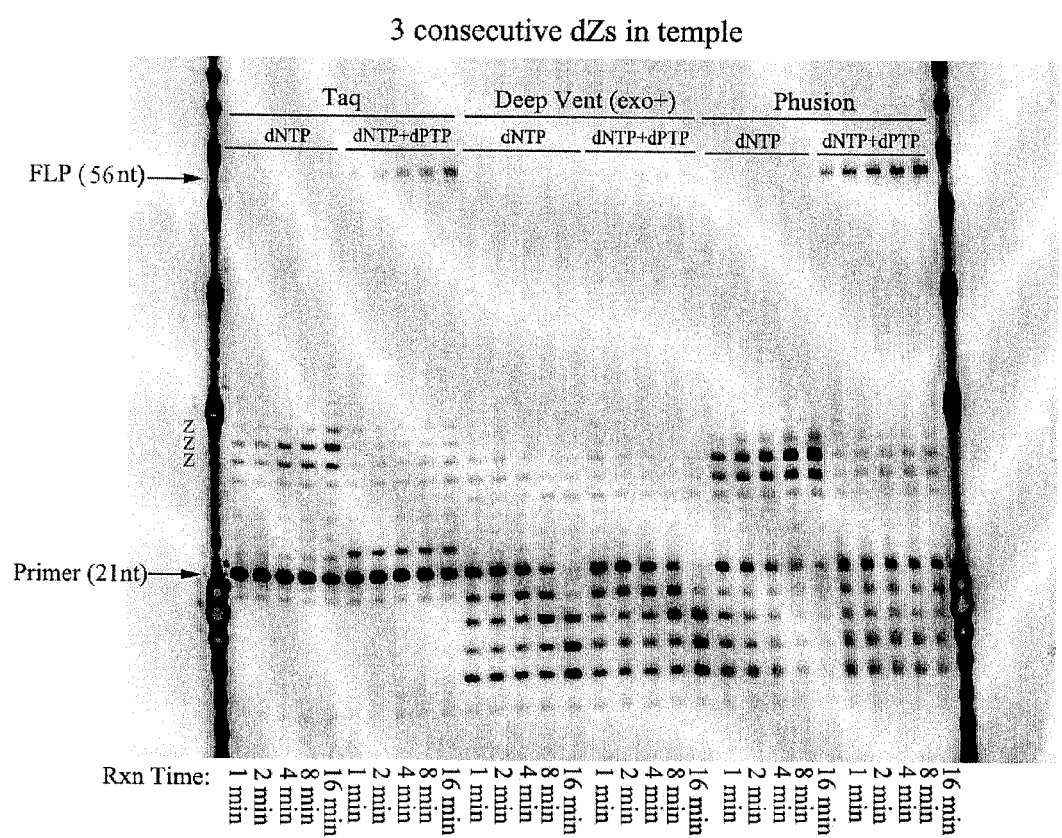
Figure 6C:
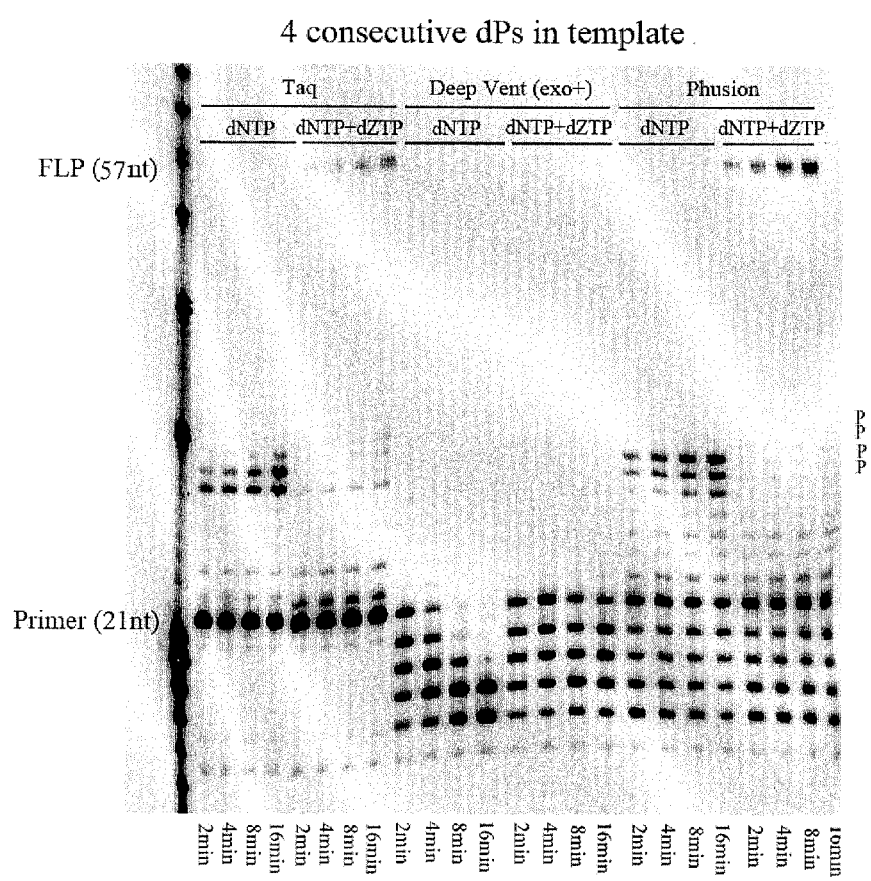
Figure 6C:
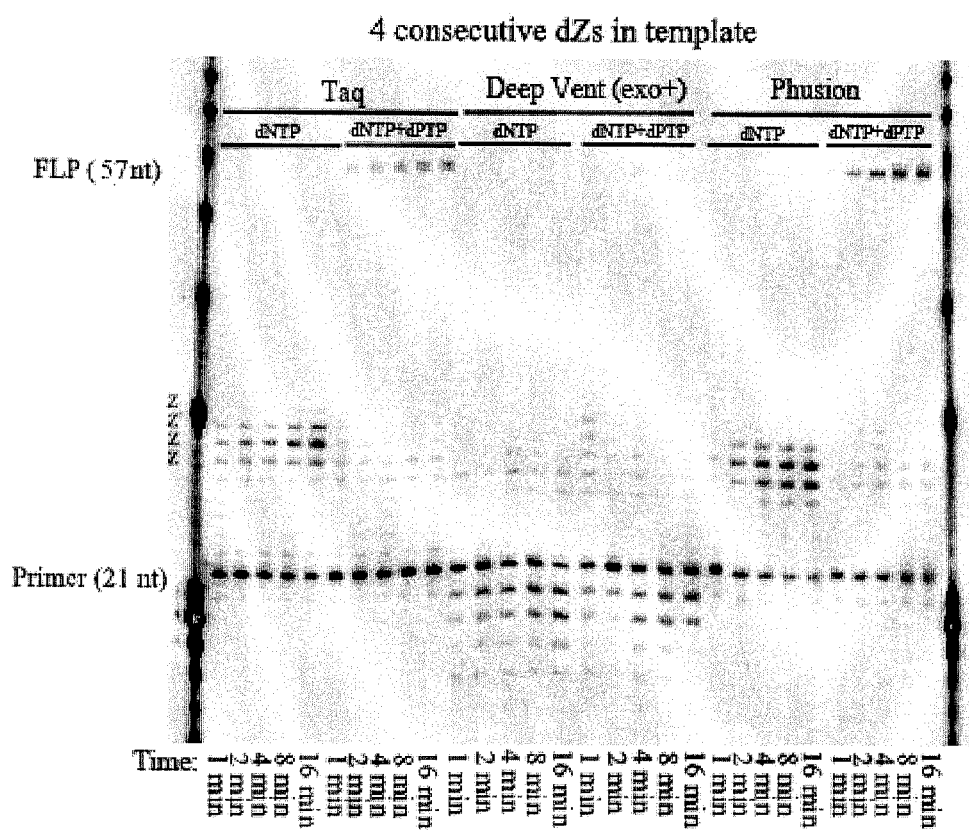

In 1× ThermoPol reaction buffer (pH 8.0 measured at 25° C.), synthetic template (Bsp-P, Table 1) or standard template (Bsp-G, Table 1) was amplified (1000 to 100000 fold, respectively) with primers (Primer-F3 and Primer-R3) and dA,T,G/TPs=0.1 mM, dCTP=0.4 mM, dZTP=0.05 mM, and dPTP=0.6 mM using JumpStart Taq DNA polymerase (0.08 unit/4, Sigma). The PCR mixture were cycled using the following conditions: one cycle of 95° C. for 1 min; followed by 31 cycles of (95° C. for 30 s, 55° C. for 30 s, 72° C. for 1 min); and finally 72° C. for 10 min. Upon the completion of PCR amplification, 1 µL of PCR mixture was digested with Bsp120I (0.5 µL, final 0.5 units/β) in 1× Buffer B at 37° C. for 20 hours (10 µL of reaction volume). Additional 0.5 µL of Bsp120I was added to the digestion mixture and incubated for another 20 hours. The digestion products were resolved on 10% PAGE gel (7 M urea) and visualized by autoradiography (see FIG. 4 for results).

Example 4

Step (d): Round of Selection

Subsequence rounds of selection were performed as described in Example 1.

Example 5

Step (e): Sequencing GACTZP DNA

Synthetic GACTZP DNA containing various numbers of Z and P nucleotides incorporated at various positions, adjacent and spaced apart (final 0.04 nM of each, see Table for sequences or Yang et al., 2011) were amplified in 1× ThermoPol reaction buffer (pH=8.0, measured at room temperature) containing primers (0.4 µM each of Primer-F1 and Primer-R1, or Primer-F2 and Primer-R2, or Primer-F3 and Primer-R3), dA,T,G/TPs (each 0.1 mM), dCTP (0.2 mM), dZTP (0.05 mM), dPTP (0.6 mM), and 0.05 unit/µL of JumpStart Taq DNA polymerase in a total volume of 50 µL. The following PCR conditions were used: one cycle of 95° C. for 1 min; followed by 21 cycles of (95° C. for 20 s, 58° C. for 25 s, 72° C. for 3 min); and finally 72° C. for 10 min. Upon the completion of the PCR, samples (10 µl) were taken from each PCR mixture, mixed with 6× agarose loading dye (2 µL, Promega), and analyzed on agarose gel.

As a first step towards sequencing, the remaining single stranded primers and excess triphosphates were degraded in the amplicon mixture by incubating aliquots (20 µL) of the PCR mixture with ExoSAP-IT (8 µL, USB, Cleveland, Ohio) at 37° C. for 30 min, and then at 80° C. for 15 min. Double stranded amplicons were then recovered by Qiaquick Nucleotide Remove Kit (Qiagen, Valencia, Calif.). The GACTZP DNA was eluted from the spin column using EB buffer (200 µL, 10 mM Tris'Cl, pH 8.5) and sequenced using the process described below.

First, the purified GACTZP DNA was amplified using JumpStart Taq DNA polymerase (0.05 unit/µL) in 1× ThermoPol reaction buffer (pH=8.8 at room temperature), 0.25 µM of each Primer (Primer-F1 and Primer-R1, or Primer-F2 and Primer-R2, or Primer-F3 and Primer-R3), four standard dNTPs (final 0.2 mM of each) and dPTP (final 0.2 mM). The following PCR conditions were used: one cycle of 95° C. for 1 min; followed by 25 cycles of (95° C. for 20 s, 58° C. for 25 s, 72° C. for 1.5 min); and finally 72° C. for 15 min. Upon the completion of PCR, PCR products were analyzed by agarose gel electrophoresis.

Fresh PCR products were cloned into the pCR® 2.1-TOPO vector and transformed the recombinant vector into One Shot® DH5α™-T1® chemically competent cells using the TOPO TA Cloning® Kits (Invitrogen, Carlsbad, Calif.). Blue-white screening gave 24 to 40 colonies that were submitted for Sanger sequencing (BioBasic, Canada). The sequence results are shown below.

Control Experiment

A set of 30 amplicons obtained by PCR amplification of a standard oligonucleotide (BspC) in the presence of dZTP and dPTP were sequenced. The sequences returned were nearly entirely identical to the sequence of BspC; almost no mutations arose in the presence of dZTP and dPTP, a result consistent with the data reported above obtained by restriction digestion. The output sequences ("Out") and the number of times the indicated nucleotide were found at each site are shown below

```
                                              SEQ ID NO 37
BspC:  T  G  A  G  G  G C  C  C     G     G T  A -3'

SEQ ID NO 38
Out:   T  G  A  G  G  G C  C  C/T  G/T    G T  A -3'

No:   30 30 30 30 30 30 30 30 29/1 29/1  30 30 30
```

Sequencing Results after Conversion of Z into C and T, and P into G and A

To demonstrate the ability of the conversion process to determine the sequence of DNA containing D, PCR was applied to a series of DNA molecules containing one or more Z:P pairs in the presence of dZTP and dPTP. Then, the Z:P pairs were converted into C:G pairs and T:A pairs by adding only dNTPs and dPTP. Again, ca. 30 amplicons were sequenced. The results, shown below, found a mixture of C and T at sites that contained Z in the parent DNA molecule. For sites containing GACT in the parent, GATC was returned for (nearly) all amplicons.

```
                                                                    SEQ ID NO 39
Bsp-Z:  T    G    A   G   G   G   C   C    Z      G    G    T    A

SEQ ID NO 40
Out:    T    G/A  A   G   G   G   C   C    C/T    G    G    T    A

No:    29   28/1 29  29  29  29  29  29   17/12  29   29   29   29

SEQ ID NO 41
ZZ-2P:  C    P    T   C   A   C   Z   Z    A      G    T    G    C    P    A    C
```

-continued

| | | | | | | | | | | | | | | | | |
|---|---|---|---|---|---|---|---|---|---|---|---|---|---|---|---|---|
| Out: | C | G/A | T | C | A | C/T | C/T | C/T | A | G | T | G | C | G/A | A | C |
| No: | 35 | 17/18 | 35 | 35 | 35 | 34/1 | 27/8 | 24/11 | 35 | 35 | 35 | 35 | 35 | 16/19 | 35 | 35 |

SEQ ID NO 42

| | | | | | | | | | | | | | | | | | |
|---|---|---|---|---|---|---|---|---|---|---|---|---|---|---|---|---|---|
| PP-2Z: | 5'- ...... | A | G | T | Z | G | C | A | C | T | P | P | G | T | G | A | Z | G | A |

SEQ ID NO 43

| | | | | | | | | | | | | | | | | | |
|---|---|---|---|---|---|---|---|---|---|---|---|---|---|---|---|---|---|
| Out: | 5'- ...... | A | G | T | C/T | G/A | C | A/G | C/A | T | G/A | G/A | G | T | G | A | C/T | G | A |

SEQ ID NO 44

| | | | | | | | | | | | | | | | | | |
|---|---|---|---|---|---|---|---|---|---|---|---|---|---|---|---|---|---|
| No: | | | | 22 | 22 | 22 | 16/6 | 21/1 | 22 | 20/2 | 21/1 | 22 | 18/4 | 19/3 | 22 | 22 | 22 | 22 | 9/13 | 22 | 22 |

SEQ ID NO 45

| | | | | | | | | | | | | |
|---|---|---|---|---|---|---|---|---|---|---|---|---|
| 3P-Temp: | A | C | A | C | T | P | P | P | T | A | C | T | C | A |

SEQ ID NO 46

| | | | | | | | | | | | | |
|---|---|---|---|---|---|---|---|---|---|---|---|---|
| Out: | A | C | A | C | T | G/A | G/A | G/A | T | A | C | T | C/A | A |
| No: | 22 | 22 | 22 | 22 | 22 | 17/5 | 19/3 | 16/6 | 22 | 22 | 22 | 22 | 21/1 | 22 |

SEQ ID NO 47

| | | | | | | | | | | | | | |
|---|---|---|---|---|---|---|---|---|---|---|---|---|---|
| 4-Temp: | C | A | A | C | T | P | P | P | P | T | A | C | T | C | A |

SEQ ID NO 48

| | | | | | | | | | | | | | |
|---|---|---|---|---|---|---|---|---|---|---|---|---|---|
| Out: | A | C | A | C | T | G/A | G/A | G/A | G/A | T | A | C | T | C | A/C |
| In: | 22 | 22 | 22 | 22 | 22 | 18/4 | 17/4 | 18/4 | 13/9 | 22 | 22 | 22 | 22 | 22 | 21/1 |

---

What is claimed is:

1. A process for extracting from a candidate mixture of oligonucleotide molecules, whose members have unknown sequences, specific oligonucleotide molecules that bind to a preselected target, said specific molecules comprising one or more non-standard nucleotides having nucleobases independently selected from the group consisting of

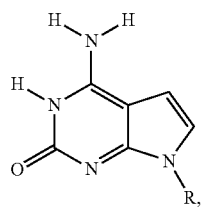 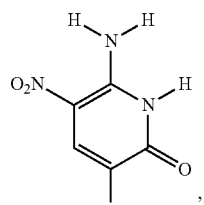 and

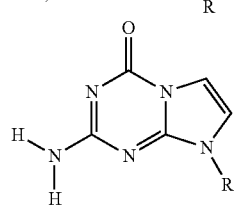

wherein said process comprises (a) obtaining a mixture of oligonucleotides having preselected regions containing, at positions that are not preselected, one or more of said non-standard nucleotide analogs, (b) contacting said mixture with said target, (c) separating the oligonucleotides in said mixture having a enhanced affinity to the target molecule relative to the candidate mixture from the remainder of the oligonucleotides in the candidate mixture; and (d) amplifying the separated oligonucleotides using the polymerase chain reaction, wherein R is the point of attachment to the oligonucleotide at position 1' of the ribose or 2'-deoxyribose of said oligonucleotide.

2. The method of claim 1 further comprising step (e), which comprises repeating steps (b), (c) and (d).

3. The method of claim 1, wherein the sequence of nucleotides in the specific molecule extracted is determined.

4. The method of claim 1, wherein said oligonucleotide molecule contains at least one nucleotide having the nucleobase

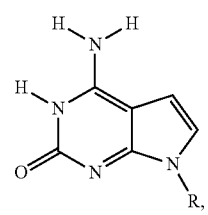

wherein R is the point of attachment to the oligonucleotide at position 1' of the ribose or 2'-deoxyribose of said oligonucleotide.

5. The method of claim 1, wherein said oligonucleotide molecule contains at least one nucleotide having the nucleobase

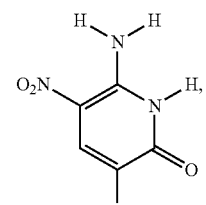

wherein R is the point of attachment to the oligonucleotide at position 1' of the ribose or 2'-deoxyribose of said oligonucleotide.

6. The method of claim 1, wherein said oligonucleotide molecule contains at least one nucleotide having the nucleobase

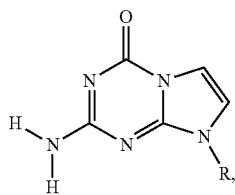

wherein R is the point of attachment to the oligonucleotide at position 1' the ribose or 2'-deoxyribose of said oligonucleotide.

7. A process for extracting from a candidate mixture or oligonucleotide molecules, whose members have unknown sequences, specific oligonucleotide molecules that catalyze a preselected chemical reaction, said specific molecules comprising one or more non-standard nucleotides having nucleobases independently selected from the group consisting of

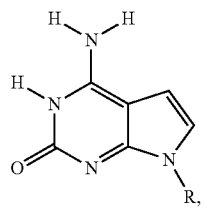 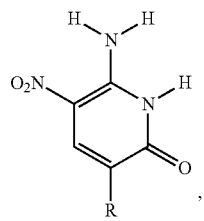 and

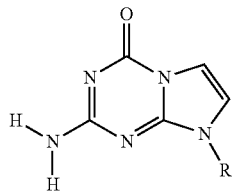

wherein said process comprises (a) obtaining a mixture of oligonucleotides containing members having preselected regions containing, at positions that are not preselected, one or more of said non-standard nucleotide analogs, (b) contacting said candidate mixture with one or more reactants for said chemical reaction, (c) separating the oligonucleotides in said mixture having a greater effectiveness to catalyze said reaction relative to the candidate mixture from the remainder of the oligonucleotides in the candidate mixture, and (d) amplifying the oligonucleotides that have enhanced catalytic effectiveness using the polymerase chain reaction, and wherein R is the point of attachment to the oligonucleotide at position 1' of the ribose or 2'-deoxyribose of said oligonucleotide.

8. The method of claim 7 further comprising step (e) which comprises repeating steps (b), (c) and (d).

9. The method of claim 7, wherein the sequence of nucleotides in the specific oligonucleotide molecule extracted is determined.

10. The method of claim 7, wherein said oligonucleotide molecule contains at least one nucleotide having the nucleobase

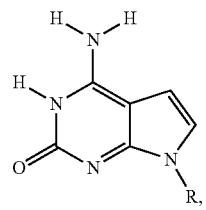

wherein R is the point of attachment to the oligonucleotide at position 1' of the ribose or 2'-deoxyribose of said oligonucleotide.

11. The method of claim 7, wherein said oligonucleotide molecule contains at least one nucleotide having the nucleobase

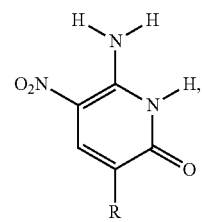

and wherein R is the point of attachment to the oligonucleotide at position 1' of the ribose or 2'-deoxyribose of said oligonucleotide.

12. The method of claim 7, wherein said oligonucleotide molecule contains at least one nucleotide having the nucleobase

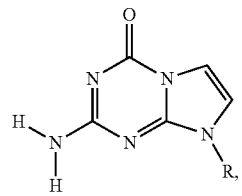

and wherein R is the point of attachment to the oligonucleotide at position 1' of the ribose or 2'-deoxyribose of said oligonucleotide.

* * * * *

SEQUENCE LISTING

```
<160> NUMBER OF SEQ IDS: 57

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
gcgaattaac cctcactaaa g                                         21

<210> SEQ ID NO 2
<211> LENGTH: 51
<212> TYPE: DNA
<213> ORGANISM: Artificial Sequence
<220> FEATURE:
<221> NAME/KEY: misc_feature
<222> LOCATION: (26)..(26)
<223> OTHER INFORMATION: n = p, nonstandard nucleotide of the invention
<220> FEATURE:
<221> NAME/KEY: misc_feature
<222> LOCATION: (27)..(27)
<223> OTHER INFORMATION: n = p, nonstandard nucleotide of the invention
<220> FEATURE:
<223> OTHER INFORMATION: Synthetic

<400> SEQUENCE: 2
gcgtaatacg actcactata gacganncta ctttagtgag ggttaattcg c         51

<210> SEQ ID NO 3
<211> LENGTH: 51
<212> TYPE: DNA
<213> ORGANISM: Artificial Sequence
<220> FEATURE:
<221> NAME/KEY: misc_feature
<222> LOCATION: (25)..(25)
<223> OTHER INFORMATION: n = z, nonstandard nucleotide of the invention
```

```
<220> FEATURE:
<221> NAME/KEY: misc_feature
<222> LOCATION: (26)..(26)
<223> OTHER INFORMATION: n = z, nonstandard nucleotide of the invention
<220> FEATURE:
<223> OTHER INFORMATION: Synthetic

<400> SEQUENCE: 3
gcgaattaac cctcactaaa gtagnntcgt ctatagtgag tcgtattacg c            51

<210> SEQ ID NO 4
<211> LENGTH: 21
<212> TYPE: DNA
<213> ORGANISM: Artificial Sequence
<220> FEATURE:
<223> OTHER INFORMATION: Synthetic

<400> SEQUENCE: 4
gcgtaatacg actcactata g                                             21

<210> SEQ ID NO 5
<211> LENGTH: 21
<212> TYPE: DNA
<213> ORGANISM: Artificial Sequence
<220> FEATURE:
<223> OTHER INFORMATION: Synthetic

<400> SEQUENCE: 5
gcgaattaac cctcactaaa g                                             21

<210> SEQ ID NO 6
<211> LENGTH: 56
<212> TYPE: DNA
<213> ORGANISM: Artificial Sequence
<220> FEATURE:
<221> NAME/KEY: misc_feature
<222> LOCATION: (27)..(27)
<223> OTHER INFORMATION: n = p, nonstandard nucleotide of the invention
<220> FEATURE:
<221> NAME/KEY: misc_feature
<222> LOCATION: (28)..(28)
<223> OTHER INFORMATION: n = p, nonstandard nucleotide of the invention
<220> FEATURE:
<221> NAME/KEY: misc_feature
<222> LOCATION: (29)..(29)
<223> OTHER INFORMATION: n = p, nonstandard nucleotide of the invention
<220> FEATURE:
<223> OTHER INFORMATION: Synthetic

<400> SEQUENCE: 6
gcgtaatacg actcactata gacactnnnt actcacttta gtgagggtta attcgc       56

<210> SEQ ID NO 7
<211> LENGTH: 56
<212> TYPE: DNA
<213> ORGANISM: Artificial Sequence
<220> FEATURE:
<221> NAME/KEY: misc_feature
<222> LOCATION: (28)..(28)
<223> OTHER INFORMATION: n = z, nonstandard nucleotide of the invention
<220> FEATURE:
<221> NAME/KEY: misc_feature
<222> LOCATION: (29)..(29)
<223> OTHER INFORMATION: n = z, nonstandard nucleotide of the invention
<220> FEATURE:
<221> NAME/KEY: misc_feature
<222> LOCATION: (30)..(30)
<223> OTHER INFORMATION: n = z, nonstandard nucleotide of the invention
<220> FEATURE:
<223> OTHER INFORMATION: Synthetic
```

```
<400> SEQUENCE: 7
gcgaattaac cctcactaaa gtgagtannn agtgtctata gtgagtcgta ttacgc        56

<210> SEQ ID NO 8
<211> LENGTH: 21
<212> TYPE: DNA
<213> ORGANISM: Artificial Sequence
<220> FEATURE:
<223> OTHER INFORMATION: Synthetic

<400> SEQUENCE: 8
gcgtaatacg actcactata g                                              21

<210> SEQ ID NO 9
<211> LENGTH: 21
<212> TYPE: DNA
<213> ORGANISM: Artificial Sequence
<220> FEATURE:
<223> OTHER INFORMATION: Synthetic

<400> SEQUENCE: 9
gcgaattaac cctcactaaa g                                              21

<210> SEQ ID NO 10
<211> LENGTH: 57
<212> TYPE: DNA
<213> ORGANISM: Artificial Sequence
<220> FEATURE:
<221> NAME/KEY: misc_feature
<222> LOCATION: (27)..(27)
<223> OTHER INFORMATION: n = p, nonstandard nucleotide of the invention
<220> FEATURE:
<221> NAME/KEY: misc_feature
<222> LOCATION: (28)..(28)
<223> OTHER INFORMATION: n = p, nonstandard nucleotide of the invention
<220> FEATURE:
<221> NAME/KEY: misc_feature
<222> LOCATION: (29..(29)
<223> OTHER INFORMATION: n = p, nonstandard nucleotide of the invention
<220> FEATURE:
<221> NAME/KEY: misc_feature
<222> LOCATION: (30)..(30)
<223> OTHER INFORMATION: n = p, nonstandard nucleotide of the invention
<220> FEATURE:
<223> OTHER INFORMATION: Synthetic

<400> SEQUENCE: 10
gcgtaatacg actcactata gacactnnnn tactcacttt agtgagggtt aattcgc       57

<210> SEQ ID NO 11
<211> LENGTH: 57
<212> TYPE: DNA
<213> ORGANISM: Artificial Sequence
<220> FEATURE:
<221> NAME/KEY: misc_feature
<222> LOCATION: (28)..(28)
<223> OTHER INFORMATION: n = z, nonstandard nucleotide of the invention
<220> FEATURE:
<221> NAME/KEY: misc_feature
<222> LOCATION: (29)..(29)
<223> OTHER INFORMATION: n = z, nonstandard nucleotide of the invention
<220> FEATURE:
<221> NAME/KEY: misc_feature
<222> LOCATION: (30)..(30)
<223> OTHER INFORMATION: n = z, nonstandard nucleotide of the invention
<220> FEATURE:
<221> NAME/KEY: misc_feature
<222> LOCATION: (31)..(31)
<223> OTHER INFORMATION: n = z, nonstandard nucleotide of the invention
<220> FEATURE:
<223> OTHER INFORMATION: Synthetic
```

```
<400> SEQUENCE: 11
gcgaattaac cctcactaaa gtgagtannn nagtgtctat agtgagtcgt attacgc        57

<210> SEQ ID NO 12
<211> LENGTH: 21
<212> TYPE: DNA
<213> ORGANISM: Artificial Sequence
<220> FEATURE:
<223> OTHER INFORMATION: Synthetic

<400> SEQUENCE: 12
gcgtaatacg actcactata g                                              21

<210> SEQ ID NO 13
<211> LENGTH: 21
<212> TYPE: DNA
<213> ORGANISM: Artificial Sequence
<220> FEATURE:
<223> OTHER INFORMATION: Synthetic

<400> SEQUENCE: 13
gcgaattaac cctcactaaa g                                              21

<210> SEQ ID NO 14
<211> LENGTH: 51
<212> TYPE: DNA
<213> ORGANISM: Artificial Sequence
<220> FEATURE:
<223> OTHER INFORMATION: Synthetic

<400> SEQUENCE: 14
gcgtaatacg actcactata gacgaggcta ctttagtgag ggttaattcg c             51

<210> SEQ ID NO 15
<211> LENGTH: 51
<212> TYPE: DNA
<213> ORGANISM: Artificial Sequence
<220> FEATURE:
<221> NAME/KEY: misc_feature
<222> LOCATION: (26)..(26)
<223> OTHER INFORMATION: n = p, nonstandard nucleotide of the invention
<220> FEATURE:
<223> OTHER INFORMATION: Synthetic

<400> SEQUENCE: 15
gcgtaatacg actcactata gacgancgta ctttagtgag ggttaattcg c             51

<210> SEQ ID NO 16
<211> LENGTH: 51
<212> TYPE: DNA
<213> ORGANISM: Artificial Sequence
<220> FEATURE:
<221> NAME/KEY: misc_feature
<222> LOCATION: (26)..(26)
<223> OTHER INFORMATION: n = p, nonstandard nucleotide of the invention
<220> FEATURE:
<221> NAME/KEY: misc_feature
<222> LOCATION: (27)..(27)
<223> OTHER INFORMATION: n = p, nonstandard nucleotide of the invention
<220> FEATURE:
<223> OTHER INFORMATION: Synthetic

<400> SEQUENCE: 16
gcgtaatacg actcactata gacganncta ctttagtgag ggttaattcg c             51
```

```
<210> SEQ ID NO 17
<211> LENGTH: 56
<212> TYPE: DNA
<213> ORGANISM: Artificial Sequence
<220> FEATURE:
<221> NAME/KEY: misc_feature
<222> LOCATION: (27)..(27)
<223> OTHER INFORMATION: n = p, nonstandard nucleotide of the invention
<220> FEATURE:
<221> NAME/KEY: misc_feature
<222> LOCATION: (28)..(28)
<223> OTHER INFORMATION: n = p, nonstandard nucleotide of the invention
<220> FEATURE:
<221> NAME/KEY: misc_feature
<222> LOCATION: (29)..(29)
<223> OTHER INFORMATION: n = p, nonstandard nucleotide of the invention
<220> FEATURE:
<223> OTHER INFORMATION: Synthetic

<400> SEQUENCE: 17
gcgtaatacg actcactata gacactnnnt actcacttta gtgagggtta attcgc        56

<210> SEQ ID NO 18
<211> LENGTH: 57
<212> TYPE: DNA
<213> ORGANISM: Artificial Sequence
<220> FEATURE:
<221> NAME/KEY: misc_feature
<222> LOCATION: (27)..(27)
<223> OTHER INFORMATION: n = p, nonstandard nucleotide of the invention
<220> FEATURE:
<221> NAME/KEY: misc_feature
<222> LOCATION: (28)..(28)
<223> OTHER INFORMATION: n = p, nonstandard nucleotide of the invention
<220> FEATURE:
<221> NAME/KEY: misc_feature
<222> LOCATION: (29)..(29)
<223> OTHER INFORMATION: n = p, nonstandard nucleotide of the invention
<220> FEATURE:
<221> NAME/KEY: misc_feature
<222> LOCATION: (30)..(30)
<223> OTHER INFORMATION: n = p, nonstandard nucleotide of the invention
<220> FEATURE:
<223> OTHER INFORMATION: Synthetic

<400> SEQUENCE: 18
gcgtaatacg actcactata gacactnnnn tactcacttt agtgagggtt aattcgc       57

<210> SEQ ID NO 19
<211> LENGTH: 57
<212> TYPE: DNA
<213> ORGANISM: Artificial Sequence
<220> FEATURE:
<221> NAME/KEY: misc_feature
<222> LOCATION: (27)..(27)
<223> OTHER INFORMATION: n = g, nonstandard nucleotide of the invention
<220> FEATURE:
<221> NAME/KEY: misc_feature
<222> LOCATION: (28)..(28)
<223> OTHER INFORMATION: n = g, nonstandard nucleotide of the invention
<220> FEATURE:
<221> NAME/KEY: misc_feature
<222> LOCATION: (29)..(29)
<223> OTHER INFORMATION: n = g, nonstandard nucleotide of the invention
<220> FEATURE:
<221> NAME/KEY: misc_feature
<222> LOCATION: (30)..(30)
<223> OTHER INFORMATION: n = g, nonstandard nucleotide of the invention
<220> FEATURE:
<223> OTHER INFORMATION: Synthetic

<400> SEQUENCE: 19
gcgtaatacg actcactata gacactnnnn tactcacttt agtgagggtt aattcgc       57
```

```
<210> SEQ ID NO 20
<211> LENGTH: 51
<212> TYPE: DNA
<213> ORGANISM: Artificial Sequence
<220> FEATURE:
<221> NAME/KEY: misc_feature
<222> LOCATION: (25)..(25)
<223> OTHER INFORMATION: n = c, nonstandard nucleotide of the invention
<220> FEATURE:
<221> NAME/KEY: misc_feature
<222> LOCATION: (26)..(26)
<223> OTHER INFORMATION: n = c, nonstandard nucleotide of the invention
<220> FEATURE:
<223> OTHER INFORMATION: Synthetic

<400> SEQUENCE: 20
gcgaattaac cctcactaaa gtagnntcgt ctatagtgag tcgtattacg c          51

<210> SEQ ID NO 21
<211> LENGTH: 51
<212> TYPE: DNA
<213> ORGANISM: Artificial Sequence
<220> FEATURE:
<221> NAME/KEY: misc_feature
<222> LOCATION: (26)..(26)
<223> OTHER INFORMATION: n = z, nonstandard nucleotide of the invention
<220> FEATURE:
<223> OTHER INFORMATION: Synthetic

<400> SEQUENCE: 21
gcgaattaac cctcactaaa gtacgntcgt ctatagtgag tcgtattacg c          51

<210> SEQ ID NO 22
<211> LENGTH: 51
<212> TYPE: DNA
<213> ORGANISM: Artificial Sequence
<220> FEATURE:
<221> NAME/KEY: misc_feature
<222> LOCATION: (25)..(25)
<223> OTHER INFORMATION: n = z, nonstandard nucleotide of the invention
<220> FEATURE:
<221> NAME/KEY: misc_feature
<222> LOCATION: (26)..(26)
<223> OTHER INFORMATION: n = z, nonstandard nucleotide of the invention
<220> FEATURE:
<223> OTHER INFORMATION: Synthetic

<400> SEQUENCE: 22
gcgaattaac cctcactaaa gtagnntcgt ctatagtgag tcgtattacg c          51

<210> SEQ ID NO 23
<211> LENGTH: 56
<212> TYPE: DNA
<213> ORGANISM: Artificial Sequence
<220> FEATURE:
<221> NAME/KEY: misc_feature
<222> LOCATION: (28)..(28)
<223> OTHER INFORMATION: n = z, nonstandard nucleotide of the invention
<220> FEATURE:
<221> NAME/KEY: misc_feature
<222> LOCATION: (29)..(29)
<223> OTHER INFORMATION: n = z, nonstandard nucleotide of the invention
<220> FEATURE:
<221> NAME/KEY: misc_feature
<222> LOCATION: (30)..(30)
<223> OTHER INFORMATION: n = z, nonstandard nucleotide of the invention
<220> FEATURE:
<223> OTHER INFORMATION: Synthetic

<400> SEQUENCE: 23
gcgaattaac cctcactaaa gtgagtannn agtgtctata gtgagtcgta ttacgc     56
```

```
<210> SEQ ID NO 24
<211> LENGTH: 57
<212> TYPE: DNA
<213> ORGANISM: Artificial Sequence
<220> FEATURE:
<221> NAME/KEY: misc_feature
<222> LOCATION: (28)..(28)
<223> OTHER INFORMATION: n = z, nonstandard nucleotide of the invention
<220> FEATURE:
<221> NAME/KEY: misc_feature
<222> LOCATION: (29)..(29)
<223> OTHER INFORMATION: n = z, nonstandard nucleotide of the invention
<220> FEATURE:
<221> NAME/KEY: misc_feature
<222> LOCATION: (30)..(30)
<223> OTHER INFORMATION: n = z, nonstandard nucleotide of the invention
<220> FEATURE:
<221> NAME/KEY: misc_feature
<222> LOCATION: (31)..(31)
<223> OTHER INFORMATION: n = z, nonstandard nucleotide of the invention
<220> FEATURE:
<223> OTHER INFORMATION: Synthetic

<400> SEQUENCE: 24
gcgaattaac cctcactaaa gtgagtannn nagtgtctat agtgagtcgt attacgc      57

<210> SEQ ID NO 25
<211> LENGTH: 57
<212> TYPE: DNA
<213> ORGANISM: Artificial Sequence
<220> FEATURE:
<221> NAME/KEY: misc_feature
<222> LOCATION: (28)..(28)
<223> OTHER INFORMATION: n = c, nonstandard nucleotide of the invention
<220> FEATURE:
<221> NAME/KEY: misc_feature
<222> LOCATION: (29)..(29)
<223> OTHER INFORMATION: n = c, nonstandard nucleotide of the invention
<220> FEATURE:
<221> NAME/KEY: misc_feature
<222> LOCATION: (30)..(30)
<223> OTHER INFORMATION: n = c, nonstandard nucleotide of the invention
<220> FEATURE:
<221> NAME/KEY: misc_feature
<222> LOCATION: (31)..(31)
<223> OTHER INFORMATION: n = c, nonstandard nucleotide of the invention
<220> FEATURE:
<223> OTHER INFORMATION: Synthetic

<400> SEQUENCE: 25
gcgaattaac cctcactaaa gtgagtannn nagtgtctat agtgagtcgt attacgc      57

<210> SEQ ID NO 26
<211> LENGTH: 21
<212> TYPE: DNA
<213> ORGANISM: Artificial Sequence
<220> FEATURE:
<223> OTHER INFORMATION: Synthetic

<400> SEQUENCE: 26
gcgtaatacg actcactata g                                             21

<210> SEQ ID NO 27
<211> LENGTH: 24
<212> TYPE: DNA
<213> ORGANISM: Artificial Sequence
<220> FEATURE:
<223> OTHER INFORMATION: Synthetic

<400> SEQUENCE: 27
tcgcacacag gaaacagcta tgac                                          24
```

```
<210> SEQ ID NO 28
<211> LENGTH: 73
<212> TYPE: DNA
<213> ORGANISM: Artificial Sequence
<220> FEATURE:
<221> NAME/KEY: misc_feature
<222> LOCATION: (31)..(31)
<223> OTHER INFORMATION: n = p, nonstandard nucleotide of the invention
<220> FEATURE:
<221> NAME/KEY: misc_feature
<222> LOCATION: (36)..(36)
<223> OTHER INFORMATION: n = z, nonstandard nucleotide of the invention
<220> FEATURE:
<221> NAME/KEY: misc_feature
<222> LOCATION: (37)..(37)
<223> OTHER INFORMATION: n = z, nonstandard nucleotide of the invention
<220> FEATURE:
<221> NAME/KEY: misc_feature
<222> LOCATION: (43)..(43)
<223> OTHER INFORMATION: n = p, nonstandard nucleotide of the invention
<220> FEATURE:
<223> OTHER INFORMATION: Synthetic

<400> SEQUENCE: 28
gacactagta gcactcacta tacgtgactc ntcacnnagt gcnactacgg tcatagctgt      60
ttcctgtgtg cga                                                        73

<210> SEQ ID NO 29
<211> LENGTH: 73
<212> TYPE: DNA
<213> ORGANISM: Artificial Sequence
<220> FEATURE:
<221> NAME/KEY: misc_feature
<222> LOCATION: (31)..(31)
<223> OTHER INFORMATION: n = z, nonstandard nucleotide of the invention
<220> FEATURE:
<221> NAME/KEY: misc_feature
<222> LOCATION: (37)..(37)
<223> OTHER INFORMATION: n = p, nonstandard nucleotide of the invention
<220> FEATURE:
<221> NAME/KEY: misc_feature
<222> LOCATION: (38)..(38)
<223> OTHER INFORMATION: n = p, nonstandard nucleotide of the invention
<220> FEATURE:
<221> NAME/KEY: misc_feature
<222> LOCATION: (43)..(43)
<223> OTHER INFORMATION: n = z, nonstandard nucleotide of the invention
<220> FEATURE:
<223> OTHER INFORMATION: Synthetic

<400> SEQUENCE: 29
tccacacagg aaacagctat gaccgtagat ngcactnngt gangagtcac gtatagtgag      60
tgctactcgt gtc                                                        73

<210> SEQ ID NO 30
<211> LENGTH: 24
<212> TYPE: DNA
<213> ORGANISM: Artificial Sequence
<220> FEATURE:
<223> OTHER INFORMATION: Synthetic

<400> SEQUENCE: 30
gacactagta gcactcacta tacg                                            24

<210> SEQ ID NO 31
<211> LENGTH: 24
<212> TYPE: DNA
<213> ORGANISM: Artificial Sequence
<220> FEATURE:
<223> OTHER INFORMATION: Synthetic
```

-continued

<400> SEQUENCE: 31
caggaaggag cgatcgcaac gtat                                          24

<210> SEQ ID NO 32
<211> LENGTH: 72
<212> TYPE: DNA
<213> ORGANISM: Artificial Sequence
<220> FEATURE:
<221> NAME/KEY: misc_feature
<222> LOCATION: (38)..(38)
<223> OTHER INFORMATION: n = z, nonstandard nucleotide of the invention
<220> FEATURE:
<223> OTHER INFORMATION: Synthetic

<400> SEQUENCE: 32
ctaggacgac ggactgccta tgagagacat gagggccngg taccatcgat acgttgcgat    60
cgctccttcc tg                                                       72

<210> SEQ ID NO 33
<211> LENGTH: 71
<212> TYPE: DNA
<213> ORGANISM: Artificial Sequence
<220> FEATURE:
<221> NAME/KEY: misc_feature
<222> LOCATION: (34)..(34)
<223> OTHER INFORMATION: n = p, nonstandard nucleotide of the invention
<220> FEATURE:
<223> OTHER INFORMATION: Synthetic

<400> SEQUENCE: 33
caggaaggac gatcgcaacg tatcgatggt accnggccct catgtctctc ataggcagtc    60
cgtcgtccta g                                                        71

<210> SEQ ID NO 34
<211> LENGTH: 72
<212> TYPE: DNA
<213> ORGANISM: Artificial Sequence
<220> FEATURE:
<221> NAME/KEY: misc_feature
<222> LOCATION: (38)..(38)
<223> OTHER INFORMATION: n = c, nonstandard nucleotide of the invention
<220> FEATURE:
<223> OTHER INFORMATION: Synthetic

<400> SEQUENCE: 34
ctaggacgac ggactgccta tgagagacat gagggccngg taccatcgat acgttgcgat    60
cgctccttcc tg                                                       72

<210> SEQ ID NO 35
<211> LENGTH: 72
<212> TYPE: DNA
<213> ORGANISM: Artificial Sequence
<220> FEATURE:
<221> NAME/KEY: misc_feature
<222> LOCATION: (35)..(35)
<223> OTHER INFORMATION: n = g, nonstandard nucleotide of the invention
<220> FEATURE:
<223> OTHER INFORMATION: Synthetic

<400> SEQUENCE: 35
caggaaggag cgatcgcaac gtatcgatgg taccnggccc tcatgtctct cataggcagt    60
ccgtcgtcct ag                                                       72

```
<210> SEQ ID NO 36
<211> LENGTH: 24
<212> TYPE: DNA
<213> ORGANISM: Artificial Sequence
<220> FEATURE:
<223> OTHER INFORMATION: Synthetic

<400> SEQUENCE: 36
ctaggacgac ggactgccta tgag                                           24

<210> SEQ ID NO 37
<211> LENGTH: 13
<212> TYPE: DNA
<213> ORGANISM: Artificial Sequence
<220> FEATURE:
<221> NAME/KEY: misc_feature
<222> LOCATION: (09)..(09)
<223> OTHER INFORMATION: n = c, nonstandard nucleotide of the invention
<220> FEATURE:
<223> OTHER INFORMATION: Synthetic

<400> SEQUENCE: 37
tgagggccng gta                                                       13

<210> SEQ ID NO 38
<211> LENGTH: 14
<212> TYPE: DNA
<213> ORGANISM: Artificial Sequence
<220> FEATURE:
<221> NAME/KEY: misc_feature
<222> LOCATION: (09)..(09)
<223> OTHER INFORMATION: n = c or t, nonstandard nucleotide of the
      invention
<220> FEATURE:
<223> OTHER INFORMATION: Synthetic

<400> SEQUENCE: 38
tgagggccng tgta                                                      14

<210> SEQ ID NO 39
<211> LENGTH: 13
<212> TYPE: DNA
<213> ORGANISM: Artificial Sequence
<220> FEATURE:
<221> NAME/KEY: misc_feature
<222> LOCATION: (09)..(09)
<223> OTHER INFORMATION: n = z, nonstandard nucleotide of the invention
<220> FEATURE:
<223> OTHER INFORMATION: Synthetic

<400> SEQUENCE: 39
tgagggccng gta                                                       13

<210> SEQ ID NO 40
<211> LENGTH: 14
<212> TYPE: DNA
<213> ORGANISM: Artificial Sequence
<220> FEATURE:
<221> NAME/KEY: misc_feature
<222> LOCATION: (10)..(10)
<223> OTHER INFORMATION: n = c or t, nonstandard nucleotide of the
      invention
<220> FEATURE:
<223> OTHER INFORMATION: Synthetic

<400> SEQUENCE: 40
tgaagggccn ggta                                                      14
```

```
<210> SEQ ID NO 41
<211> LENGTH: 16
<212> TYPE: DNA
<213> ORGANISM: Artificial Sequence
<220> FEATURE:
<221> NAME/KEY: misc_feature
<222> LOCATION: (02)..(02)
<223> OTHER INFORMATION: n = p, nonstandard nucleotide of the invention
<220> FEATURE:
<221> NAME/KEY: misc_feature
<222> LOCATION: (07)..(07)
<223> OTHER INFORMATION: n = z, nonstandard nucleotide of the invention
<220> FEATURE:
<221> NAME/KEY: misc_feature
<222> LOCATION: (08)..(08)
<223> OTHER INFORMATION: n = z, nonstandard nucleotide of the invention
<220> FEATURE:
<221> NAME/KEY: misc_feature
<222> LOCATION: (14)..(14)
<223> OTHER INFORMATION: n = p, nonstandard nucleotide of the invention
<220> FEATURE:
<223> OTHER INFORMATION: Synthetic

<400> SEQUENCE: 41
cntcacnnag tgcnac                                                     16

<210> SEQ ID NO 42
<211> LENGTH: 16
<212> TYPE: DNA
<213> ORGANISM: Artificial Sequence
<220> FEATURE:
<221> NAME/KEY: misc_feature
<222> LOCATION: (02)..(02)
<223> OTHER INFORMATION: n = g or a, nonstandard nucleotide of the
      invention
<220> FEATURE:
<221> NAME/KEY: misc_feature
<222> LOCATION: (06)..(06)
<223> OTHER INFORMATION: n = c or t, nonstandard nucleotide of the
      invention
<220> FEATURE:
<221> NAME/KEY: misc_feature
<222> LOCATION: (07)..(27)
<223> OTHER INFORMATION: n = c or t, nonstandard nucleotide of the
      invention
<220> FEATURE:
<221> NAME/KEY: misc_feature
<222> LOCATION: (08)..(08)
<223> OTHER INFORMATION: n = c or t, nonstandard nucleotide of the
      invention
<220> FEATURE:
<221> NAME/KEY: misc_feature
<222> LOCATION: (14)..(14)
<223> OTHER INFORMATION: n = g or a, nonstandard nucleotide of the
      invention
<220> FEATURE:
<223> OTHER INFORMATION: Synthetic

<400> SEQUENCE: 42
cntcannnag tgcnac                                                     16

<210> SEQ ID NO 43
<211> LENGTH: 18
<212> TYPE: DNA
<213> ORGANISM: Artificial Sequence
<220> FEATURE:
<221> NAME/KEY: misc_feature
<222> LOCATION: (04)..(04)
<223> OTHER INFORMATION: n = z, nonstandard nucleotide of the invention
<220> FEATURE:
<221> NAME/KEY: misc_feature
<222> LOCATION: (10)..(10)
<223> OTHER INFORMATION: n = p, nonstandard nucleotide of the invention
```

```
<220> FEATURE:
<221> NAME/KEY: misc_feature
<222> LOCATION: (11)..(11)
<223> OTHER INFORMATION: n = p, nonstandard nucleotide of the invention
<220> FEATURE:
<221> NAME/KEY: misc_feature
<222> LOCATION: (16)..(16)
<223> OTHER INFORMATION: n = z, nonstandard nucleotide of the invention
<220> FEATURE:
<223> OTHER INFORMATION: Synthetic

<400> SEQUENCE: 43
agtngcactn ngtganga                                                  18

<210> SEQ ID NO 44
<211> LENGTH: 18
<212> TYPE: DNA
<213> ORGANISM: Artificial Sequence
<220> FEATURE:
<221> NAME/KEY: misc_feature
<222> LOCATION: (04)..(04)
<223> OTHER INFORMATION: n = c or t, nonstandard nucleotide of the
      invention
<220> FEATURE:
<221> NAME/KEY: misc_feature
<222> LOCATION: (05)..(05)
<223> OTHER INFORMATION: n = g or a, nonstandard nucleotide of the
      invention
<220> FEATURE:
<221> NAME/KEY: misc_feature
<222> LOCATION: (07)..(07)
<223> OTHER INFORMATION: n = p, nonstandard nucleotide of the invention
<220> FEATURE:
<221> NAME/KEY: misc_feature
<222> LOCATION: (08)..(08)
<223> OTHER INFORMATION: n = c or a, nonstandard nucleotide of the
      invention
<220> FEATURE:
<221> NAME/KEY: misc_feature
<222> LOCATION: (10)..(10)
<223> OTHER INFORMATION: n = g or a, nonstandard nucleotide of the
      invention
<220> FEATURE:
<221> NAME/KEY: misc_feature
<222> LOCATION: (11)..(11)
<223> OTHER INFORMATION: n = g or a, nonstandard nucleotide of the
      invention
<220> FEATURE:
<221> NAME/KEY: misc_feature
<222> LOCATION: (16)..(16)
<223> OTHER INFORMATION: n = p, nonstandard nucleotide of the invention
<220> FEATURE:
<223> OTHER INFORMATION: Synthetic

<400> SEQUENCE: 44
agtnncnntn ngtganga                                                  18

<210> SEQ ID NO 45
<211> LENGTH: 14
<212> TYPE: DNA
<213> ORGANISM: Artificial Sequence
<220> FEATURE:
<221> NAME/KEY: misc_feature
<222> LOCATION: (06)..(06)
<223> OTHER INFORMATION: n = p, nonstandard nucleotide of the invention
<220> FEATURE:
<221> NAME/KEY: misc_feature
<222> LOCATION: (07)..(07)
<223> OTHER INFORMATION: n = p, nonstandard nucleotide of the invention
<220> FEATURE:
<221> NAME/KEY: misc_feature
<222> LOCATION: (08)..(08)
<223> OTHER INFORMATION: n = p, nonstandard nucleotide of the invention
<220> FEATURE:
<223> OTHER INFORMATION: Synthetic
```

```
<400> SEQUENCE: 45
acactnnnta ctca                                                    14

<210> SEQ ID NO 46
<211> LENGTH: 14
<212> TYPE: DNA
<213> ORGANISM: Artificial Sequence
<220> FEATURE:
<221> NAME/KEY: misc_feature
<222> LOCATION: (06)..(06)
<223> OTHER INFORMATION: n = g or a, nonstandard nucleotide of the
      invention
<220> FEATURE:
<221> NAME/KEY: misc_feature
<222> LOCATION: (07)..(07)
<223> OTHER INFORMATION: n = g or a, nonstandard nucleotide of the
      invention
<220> FEATURE:
<221> NAME/KEY: misc_feature
<222> LOCATION: (08)..(08)
<223> OTHER INFORMATION: n = g or a, nonstandard nucleotide of the
      invention
<220> FEATURE:
<221> NAME/KEY: misc_feature
<222> LOCATION: (13)..(13)
<223> OTHER INFORMATION: n = p, nonstandard nucleotide of the invention
<220> FEATURE:
<223> OTHER INFORMATION: Synthetic

<400> SEQUENCE: 46
acactnnnta ctna                                                    14

<210> SEQ ID NO 47
<211> LENGTH: 15
<212> TYPE: DNA
<213> ORGANISM: Artificial Sequence
<220> FEATURE:
<221> NAME/KEY: misc_feature
<222> LOCATION: (06)..(06)
<223> OTHER INFORMATION: n = p, nonstandard nucleotide of the invention
<220> FEATURE:
<221> NAME/KEY: misc_feature
<222> LOCATION: (07)..(07)
<223> OTHER INFORMATION: n = p, nonstandard nucleotide of the invention
<220> FEATURE:
<221> NAME/KEY: misc_feature
<222> LOCATION: (08)..(08)
<223> OTHER INFORMATION: n = p, nonstandard nucleotide of the invention
<220> FEATURE:
<221> NAME/KEY: misc_feature
<222> LOCATION: (09)..(09)
<223> OTHER INFORMATION: n = p, nonstandard nucleotide of the invention
<220> FEATURE:
<223> OTHER INFORMATION: Synthetic

<400> SEQUENCE: 47
acactnnnnt actca                                                   15

<210> SEQ ID NO 48
<211> LENGTH: 15
<212> TYPE: DNA
<213> ORGANISM: Artificial Sequence
<220> FEATURE:
<221> NAME/KEY: misc_feature
<222> LOCATION: (06)..(06)
<223> OTHER INFORMATION: n = g or a, nonstandard nucleotide of the
      invention
<220> FEATURE:
<221> NAME/KEY: misc_feature
<222> LOCATION: (07)..(07)
<223> OTHER INFORMATION: n = g or a, nonstandard nucleotide of the
      invention
```

```
<220> FEATURE:
<221> NAME/KEY: misc_feature
<222> LOCATION: (08)..(08)
<223> OTHER INFORMATION: n = g or a, nonstandard nucleotide of the
      invention
<220> FEATURE:
<221> NAME/KEY: misc_feature
<222> LOCATION: (09)..(09)
<223> OTHER INFORMATION: n =g or a, nonstandard nucleotide of the
      invention
<220> FEATURE:
<221> NAME/KEY: misc_feature
<222> LOCATION: (15)..(15)
<223> OTHER INFORMATION: n = a or c, nonstandard nucleotide of the
      invention
<220> FEATURE:
<223> OTHER INFORMATION: Synthetic

<400> SEQUENCE: 48
acactnnnnt actcn                                                      15

<210> SEQ ID NO 49
<211> LENGTH: 88
<212> TYPE: DNA
<213> ORGANISM: Artificial Sequence
<220> FEATURE:
<221> NAME/KEY: misc_feature
<222> LOCATION: (20)..(20)
<223> OTHER INFORMATION: n = nonstandard nucleotide of the invention
<220> FEATURE:
<221> NAME/KEY: misc_feature
<222> LOCATION: (21)..(21)
<223> OTHER INFORMATION: n = nonstandard nucleotide of the invention
<220> FEATURE:
<221> NAME/KEY: misc_feature
<222> LOCATION: (22)..(22)
<223> OTHER INFORMATION: n = nonstandard nucleotide of the invention
<220> FEATURE:
<221> NAME/KEY: misc_feature
<222> LOCATION: (23)..(23)
<223> OTHER INFORMATION: n = nonstandard nucleotide of the invention
<220> FEATURE:
<221> NAME/KEY: misc_feature
<222> LOCATION: (24)..(24)
<223> OTHER INFORMATION: n = nonstandard nucleotide of the invention
<220> FEATURE:
<221> NAME/KEY: misc_feature
<222> LOCATION: (25)..(25)
<223> OTHER INFORMATION: n = nonstandard nucleotide of the invention
<220> FEATURE:
<221> NAME/KEY: misc_feature
<222> LOCATION: (26)..(26)
<223> OTHER INFORMATION: n = nonstandard nucleotide of the invention
<220> FEATURE:
<221> NAME/KEY: misc_feature
<222> LOCATION: (27)..(27)
<223> OTHER INFORMATION: n = nonstandard nucleotide of the invention
<220> FEATURE:
<221> NAME/KEY: misc_feature
<222> LOCATION: (28)..(28)
<223> OTHER INFORMATION: n = nonstandard nucleotide of the invention
<220> FEATURE:
<221> NAME/KEY: misc_feature
<222> LOCATION: (29)..(29)
<223> OTHER INFORMATION: n = nonstandard nucleotide of the invention
<220> FEATURE:
<221> NAME/KEY: misc_feature
<222> LOCATION: (30)..(30)
<223> OTHER INFORMATION: n = nonstandard nucleotide of the invention
<220> FEATURE:
<221> NAME/KEY: misc_feature
<222> LOCATION: (31)..(31)
<223> OTHER INFORMATION: n = nonstandard nucleotide of the invention
<220> FEATURE:
<221> NAME/KEY: misc_feature
<222> LOCATION: (32)..(32)
<223> OTHER INFORMATION: n = nonstandard nucleotide of the invention
```

```
-continued

<220> FEATURE:
<221> NAME/KEY: misc_feature
<222> LOCATION: (33)..(33)
<223> OTHER INFORMATION: n = nonstandard nucleotide of the invention
<220> FEATURE:
<221> NAME/KEY: misc_feature
<222> LOCATION: (34)..(34)
<223> OTHER INFORMATION: n = nonstandard nucleotide of the invention
<220> FEATURE:
<221> NAME/KEY: misc_feature
<222> LOCATION: (35)..(35)
<223> OTHER INFORMATION: n = nonstandard nucleotide of the invention
<220> FEATURE:
<221> NAME/KEY: misc_feature
<222> LOCATION: (36)..(36)
<223> OTHER INFORMATION: n = nonstandard nucleotide of the invention
<220> FEATURE:
<221> NAME/KEY: misc_feature
<222> LOCATION: (37)..(37)
<223> OTHER INFORMATION: n = nonstandard nucleotide of the invention
<220> FEATURE:
<221> NAME/KEY: misc_feature
<222> LOCATION: (38)..(38)
<223> OTHER INFORMATION: n = nonstandard nucleotide of the invention
<220> FEATURE:
<221> NAME/KEY: misc_feature
<222> LOCATION: (39)..(39)
<223> OTHER INFORMATION: n = nonstandard nucleotide of the invention
<220> FEATURE:
<221> NAME/KEY: misc_feature
<222> LOCATION: (40)..(40)
<223> OTHER INFORMATION: n = nonstandard nucleotide of the invention
<220> FEATURE:
<221> NAME/KEY: misc_feature
<222> LOCATION: (41)..(41)
<223> OTHER INFORMATION: n = nonstandard nucleotide of the invention
<220> FEATURE:
<221> NAME/KEY: misc_feature
<222> LOCATION: (42)..(42)
<223> OTHER INFORMATION: n = nonstandard nucleotide of the invention
<220> FEATURE:
<221> NAME/KEY: misc_feature
<222> LOCATION: (43)..(43)
<223> OTHER INFORMATION: n = nonstandard nucleotide of the invention
<220> FEATURE:
<221> NAME/KEY: misc_feature
<222> LOCATION: (44)..(44)
<223> OTHER INFORMATION: n = nonstandard nucleotide of the invention
<220> FEATURE:
<221> NAME/KEY: misc_feature
<222> LOCATION: (45)..(45)
<223> OTHER INFORMATION: n = nonstandard nucleotide of the invention
<220> FEATURE:
<221> NAME/KEY: misc_feature
<222> LOCATION: (46)..(46)
<223> OTHER INFORMATION: n = nonstandard nucleotide of the invention
<220> FEATURE:
<221> NAME/KEY: misc_feature
<222> LOCATION: (47)..(47)
<223> OTHER INFORMATION: n = nonstandard nucleotide of the invention
<220> FEATURE:
<221> NAME/KEY: misc_feature
<222> LOCATION: (48)..(48)
<223> OTHER INFORMATION: n = nonstandard nucleotide of the invention
<220> FEATURE:
<221> NAME/KEY: misc_feature
<222> LOCATION: (49)..(49)
<223> OTHER INFORMATION: n = nonstandard nucleotide of the invention
<220> FEATURE:
<221> NAME/KEY: misc_feature
<222> LOCATION: (50)..(50)
<223> OTHER INFORMATION: n = nonstandard nucleotide of the invention
<220> FEATURE:
<221> NAME/KEY: misc_feature
<222> LOCATION: (51)..(51)
<223> OTHER INFORMATION: n = nonstandard nucleotide of the invention
<220> FEATURE:
<221> NAME/KEY: misc_feature
<222> LOCATION: (52)..(52)
<223> OTHER INFORMATION: n = nonstandard nucleotide of the invention
```

```
<220> FEATURE:
<221> NAME/KEY: misc_feature
<222> LOCATION: (53)..(53)
<223> OTHER INFORMATION: n = nonstandard nucleotide of the invention
<220> FEATURE:
<221> NAME/KEY: misc_feature
<222> LOCATION: (54)..(54)
<223> OTHER INFORMATION: n = nonstandard nucleotide of the invention
<220> FEATURE:
<221> NAME/KEY: misc_feature
<222> LOCATION: (55)..(55)
<223> OTHER INFORMATION: n = nonstandard nucleotide of the invention
<220> FEATURE:
<221> NAME/KEY: misc_feature
<222> LOCATION: (56)..(56)
<223> OTHER INFORMATION: n = nonstandard nucleotide of the invention
<220> FEATURE:
<221> NAME/KEY: misc_feature
<222> LOCATION: (57)..(57)
<223> OTHER INFORMATION: n = nonstandard nucleotide of the invention
<220> FEATURE:
<221> NAME/KEY: misc_feature
<222> LOCATION: (58)..(58)
<223> OTHER INFORMATION: n = nonstandard nucleotide of the invention
<220> FEATURE:
<221> NAME/KEY: misc_feature
<222> LOCATION: (59)..(59)
<223> OTHER INFORMATION: n = nonstandard nucleotide of the invention
<220> FEATURE:
<223> OTHER INFORMATION: Synthetic

<400> SEQUENCE: 49
gtgccaagct taccgtcacn nnnnnnnnn nnnnnnnnn nnnnnnnnn nnnnnnnng        60 agatgtcgcc atctcttcct atagtgag                                      88

<210> SEQ ID NO 50
<211> LENGTH: 43
<212> TYPE: DNA
<213> ORGANISM: Artificial Sequence
<220> FEATURE:
<221> NAME/KEY: misc_feature
<222> LOCATION: (28)..(28)
<223> OTHER INFORMATION: n = a, nonstandard nucleotide of the invention
<220> FEATURE:
<223> OTHER INFORMATION: Synthetic

<400> SEQUENCE: 50
ctgcagaatt ctaatacgac tcactatngg aagagatggc gac                     43

<210> SEQ ID NO 51
<211> LENGTH: 43
<212> TYPE: DNA
<213> ORGANISM: Artificial Sequence
<220> FEATURE:
<221> NAME/KEY: misc_feature
<222> LOCATION: (28)..(28)
<223> OTHER INFORMATION: n = a, nonstandard nucleotide of the invention
<220> FEATURE:
<223> OTHER INFORMATION: Synthetic

<400> SEQUENCE: 51
ctgcagaatt ctaatacgac tcactatngg aagagatggc gac                     43

<210> SEQ ID NO 52
<211> LENGTH: 19
<212> TYPE: DNA
<213> ORGANISM: Artificial Sequence
<220> FEATURE:
<223> OTHER INFORMATION: Synthetic

<400> SEQUENCE: 52
gtgccaagct taccgtcac                                                19
```

```
<210> SEQ ID NO 53
<211> LENGTH: 19
<212> TYPE: DNA
<213> ORGANISM: Artificial Sequence
<220> FEATURE:
<223> OTHER INFORMATION: Synthetic

<400> SEQUENCE: 53
gtgccaagct taccgtcac                                                      19

<210> SEQ ID NO 54
<211> LENGTH: 15
<212> TYPE: DNA
<213> ORGANISM: Artificial Sequence
<220> FEATURE:
<223> OTHER INFORMATION: Synthetic

<400> SEQUENCE: 54
gtgccaagct taccg                                                          15

<210> SEQ ID NO 55
<211> LENGTH: 48
<212> TYPE: DNA
<213> ORGANISM: Artificial Sequence
<220> FEATURE:
<223> OTHER INFORMATION: Synthetic

<400> SEQUENCE: 55
gagatgtcgc catctcttcc tatagtgagt cgtattagaa ttctgcag                      48

<210> SEQ ID NO 56
<211> LENGTH: 43
<212> TYPE: DNA
<213> ORGANISM: Artificial Sequence
<220> FEATURE:
<221> NAME/KEY: misc_feature
<222> LOCATION: (28)..(28)
<223> OTHER INFORMATION: n = a, nonstandard nucleotide of the invention
<220> FEATURE:
<223> OTHER INFORMATION: Synthetic

<400> SEQUENCE: 56
ctgcagaatt ctaatacgac tcactatngg aagagatggc gac                           43

<210> SEQ ID NO 57
<211> LENGTH: 88
<212> TYPE: DNA
<213> ORGANISM: Artificial Sequence
<220> FEATURE:
<221> NAME/KEY: misc_feature
<222> LOCATION: (20)..(20)
<223> OTHER INFORMATION: n = z or p, nonstandard nucleotide of the
      invention
<220> FEATURE:
<221> NAME/KEY: misc_feature
<222> LOCATION: (21)..(21)
<223> OTHER INFORMATION: n = z or p, nonstandard nucleotide of the
      invention
<220> FEATURE:
<221> NAME/KEY: misc_feature
<222> LOCATION: (22)..(22)
<223> OTHER INFORMATION: n = z or p, nonstandard nucleotide of the
      invention
<220> FEATURE:
<221> NAME/KEY: misc_feature
<222> LOCATION: (23)..(23)
<223> OTHER INFORMATION: n = z or p, nonstandard nucleotide of the
      invention
```

```
<220> FEATURE:
<221> NAME/KEY: misc_feature
<222> LOCATION: (24)..(24)
<223> OTHER INFORMATION: n = z or p, nonstandard nucleotide of the
      invention
<220> FEATURE:
<221> NAME/KEY: misc_feature
<222> LOCATION: (25)..(25)
<223> OTHER INFORMATION: n = z or p, nonstandard nucleotide of the
      invention
<220> FEATURE:
<221> NAME/KEY: misc_feature
<222> LOCATION: (26)..(26)
<223> OTHER INFORMATION: n = z or p, nonstandard nucleotide of the
      invention
<220> FEATURE:
<221> NAME/KEY: misc_feature
<222> LOCATION: (27)..(27)
<223> OTHER INFORMATION: n = z or p, nonstandard nucleotide of the
      invention
<220> FEATURE:
<221> NAME/KEY: misc_feature
<222> LOCATION: (28)..(28)
<223> OTHER INFORMATION: n = z or p, nonstandard nucleotide of the
      invention
<220> FEATURE:
<221> NAME/KEY: misc_feature
<222> LOCATION: (29)..(29)
<223> OTHER INFORMATION: n = z or p, nonstandard nucleotide of the
      invention
<220> FEATURE:
<221> NAME/KEY: misc_feature
<222> LOCATION: (30)..(30)
<223> OTHER INFORMATION: n = z or p, nonstandard nucleotide of the
      invention
<220> FEATURE:
<221> NAME/KEY: misc_feature
<222> LOCATION: (31)..(31)
<223> OTHER INFORMATION: n = z or p, nonstandard nucleotide of the
      invention
<220> FEATURE:
<221> NAME/KEY: misc_feature
<222> LOCATION: (32)..(32)
<223> OTHER INFORMATION: n = z or p, nonstandard nucleotide of the
      invention
<220> FEATURE:
<221> NAME/KEY: misc_feature
<222> LOCATION: (33)..(33)
<223> OTHER INFORMATION: n = z or p, nonstandard nucleotide of the
      invention
<220> FEATURE:
<221> NAME/KEY: misc_feature
<222> LOCATION: (34)..(34)
<223> OTHER INFORMATION: n = z or p, nonstandard nucleotide of the
      invention
<220> FEATURE:
<221> NAME/KEY: misc_feature
<222> LOCATION: (35)..(35)
<223> OTHER INFORMATION: n = z or p, nonstandard nucleotide of the
      invention
<220> FEATURE:
<221> NAME/KEY: misc_feature
<222> LOCATION: (36)..(36)
<223> OTHER INFORMATION: n = z or p, nonstandard nucleotide of the
      invention
<220> FEATURE:
<221> NAME/KEY: misc_feature
<222> LOCATION: (37)..(37)
<223> OTHER INFORMATION: n = z or p, nonstandard nucleotide of the
      invention
<220> FEATURE:
<221> NAME/KEY: misc_feature
<222> LOCATION: (38)..(38)
<223> OTHER INFORMATION: n = z or p, nonstandard nucleotide of the
      invention
<220> FEATURE:
<221> NAME/KEY: misc_feature
<222> LOCATION: (39)..(39)
<223> OTHER INFORMATION: n = z or p, nonstandard nucleotide of the
      invention
```

```
<220> FEATURE:
<221> NAME/KEY: misc_feature
<222> LOCATION: (40)..(40)
<223> OTHER INFORMATION: n = z or p, nonstandard nucleotide of the
      invention
<220> FEATURE:
<221> NAME/KEY: misc_feature
<222> LOCATION: (41)..(41)
<223> OTHER INFORMATION: n = z or p, nonstandard nucleotide of the
      invention
<220> FEATURE:
<221> NAME/KEY: misc_feature
<222> LOCATION: (42)..(42)
<223> OTHER INFORMATION: n = z or p, nonstandard nucleotide of the
      invention
<220> FEATURE:
<221> NAME/KEY: misc_feature
<222> LOCATION: (43)..(43)
<223> OTHER INFORMATION: n = z or p, nonstandard nucleotide of the
      invention
<220> FEATURE:
<221> NAME/KEY: misc_feature
<222> LOCATION: (44)..(44)
<223> OTHER INFORMATION: n = z or p, nonstandard nucleotide of the
      invention
<220> FEATURE:
<221> NAME/KEY: misc_feature
<222> LOCATION: (45)..(45)
<223> OTHER INFORMATION: n = z or p, nonstandard nucleotide of the
      invention
<220> FEATURE:
<221> NAME/KEY: misc_feature
<222> LOCATION: (46)..(46)
<223> OTHER INFORMATION: n = z or p, nonstandard nucleotide of the
      invention
<220> FEATURE:
<221> NAME/KEY: misc_feature
<222> LOCATION: (47)..(47)
<223> OTHER INFORMATION: n = z or p, nonstandard nucleotide of the
      invention
<220> FEATURE:
<221> NAME/KEY: misc_feature
<222> LOCATION: (48)..(48)
<223> OTHER INFORMATION: n = z or p, nonstandard nucleotide of the
      invention
<220> FEATURE:
<221> NAME/KEY: misc_feature
<222> LOCATION: (49)..(49)
<223> OTHER INFORMATION: n = z or p, nonstandard nucleotide of the
      invention
<220> FEATURE:
<221> NAME/KEY: misc_feature
<222> LOCATION: (50)..(50)
<223> OTHER INFORMATION: n = z or p,  nonstandard nucleotide of the
      invention
<220> FEATURE:
<221> NAME/KEY: misc_feature
<222> LOCATION: (51)..(51)
<223> OTHER INFORMATION: n = z or p, nonstandard nucleotide of the
      invention
<220> FEATURE:
<221> NAME/KEY: misc_feature
<222> LOCATION: (52)..(52)
<223> OTHER INFORMATION: n = z or p, nonstandard nucleotide of the
      invention
<220> FEATURE:
<221> NAME/KEY: misc_feature
<222> LOCATION: (53)..(53)
<223> OTHER INFORMATION: n = z or p, nonstandard nucleotide of the
      invention
<220> FEATURE:
<221> NAME/KEY: misc_feature
<222> LOCATION: (54)..(54)
<223> OTHER INFORMATION: n = z or p, nonstandard nucleotide of the
      invention
<220> FEATURE:
<221> NAME/KEY: misc_feature
<222> LOCATION: (55)..(55)
<223> OTHER INFORMATION: n = z or p, nonstandard nucleotide of the
      invention
```

```
<220> FEATURE:
<221> NAME/KEY: misc_feature
<222> LOCATION: (56)..(56)
<223> OTHER INFORMATION: n = z or p, nonstandard nucleotide of the
      invention
<220> FEATURE:
<221> NAME/KEY: misc_feature
<222> LOCATION: (57)..(57)
<223> OTHER INFORMATION: n = z or p, nonstandard nucleotide of the
      invention
<220> FEATURE:
<221> NAME/KEY: misc_feature
<222> LOCATION: (58)..(58)
<223> OTHER INFORMATION: n = z or p, nonstandard nucleotide of the
      invention
<220> FEATURE:
<221> NAME/KEY: misc_feature
<222> LOCATION: (59)..(59)
<223> OTHER INFORMATION: n = either a standard nucleotide or a
      nonstandard nucleotide of the invention
<220> FEATURE:
<223> OTHER INFORMATION: Synthetic

<400> SEQUENCE: 57
gtgccaagct taccgtcacn nnnnnnnnn nnnnnnnnn nnnnnnnnn nnnnnnnng     60 agatgtcgcc atctcttcct atagtgag                                    88
```